United States Patent [19]

Tang et al.

[11] Patent Number: 5,681,819
[45] Date of Patent: Oct. 28, 1997

[54] METHOD AND COMPOSITIONS FOR REDUCING CHOLESTEROL ABSORPTION

[75] Inventors: Jordan J. N. Tang, Edmund; Chi-Sun Wang, Oklahoma City, both of Okla.

[73] Assignee: Oklahoma Medical Research Foundation, Oklahoma City, Okla.

[21] Appl. No.: 479,160

[22] Filed: Jun. 7, 1995

Related U.S. Application Data

[63] Continuation-in-part of Ser. No. 347,718, Dec. 1, 1994.
[51] Int. Cl.$^6$ .................. A61K 38/08; A61K 38/10; A61K 38/16
[52] U.S. Cl. .................. 514/12; 514/13; 514/14; 514/15; 514/16; 514/17; 514/18
[58] Field of Search .................. 514/12, 13, 14, 514/15, 16, 17, 18

[56] References Cited

U.S. PATENT DOCUMENTS

| | | | |
|---|---|---|---|
| Re. 33,885 | 4/1992 | Mattson | 514/53 |
| 4,602,003 | 7/1986 | Malinow | 514/26 |
| 4,944,944 | 7/1990 | Tang et al. | 424/94.6 |
| 4,976,968 | 12/1990 | Steiner | 424/491 |
| 5,017,565 | 5/1991 | Lange, III et al. | 514/54 |
| 5,063,210 | 11/1991 | Lange, III et al. | 514/54 |
| 5,173,408 | 12/1992 | Lange, III et al. | 435/69.1 |
| 5,200,183 | 4/1993 | Tang et al. | 424/94.6 |
| 5,376,640 | 12/1994 | Miyazaki et al. | 514/12 |
| 5,519,001 | 5/1996 | Kushwaha et al. | 514/12 |

FOREIGN PATENT DOCUMENTS

| | | |
|---|---|---|
| 0 333 523 | 9/1989 | European Pat. Off. . |
| WO 89/08465 | 9/1989 | WIPO . |
| WO 91/06286 | 5/1991 | WIPO . |
| WO 91/06287 | 5/1991 | WIPO . |
| WO 91/15234 | 10/1991 | WIPO . |
| WO94/20610 | 7/1994 | WIPO . |
| WO96/17054 | 6/1996 | WIPO . |

OTHER PUBLICATIONS

Bierman, E.L., "Disorders of the Vascular System: Atherosclerosis and Other Forms of Arteriosclerosis," in *Harrison's Principles of Internal Medicine* 1014–1024, (E. Braunwald et al. (1987).

Bitter G.A., et al., "Expression and Secretion Vectors for Yeast," *Methods in Enzymology* (Wu and Grossman, eds.) 153:516–544 (1987).

Bosner, et al., "Assessment of percent cholesterol absorption in humans with stable isotopes," *J. of Lipid Res.* 34:1047 (1993).

Baba, I, et al., "Structure of Human Milk Bile Salt Activated Lipase," *Biochemistry* 30:500–610 (1991).

Barr, et al., "Protocol for Efficient Secretion of HSA Developed from *Pichia pastoris*," *Pharmaceutical Engineering* 12:48-51 (1992).

Bevington, P.R., "Propagation of Errors," *Data Reduction and Error Analysis for the Physical Sciences*, 56–65 and 204–246, McGraw–Hill, New York (1969)*.

Bosner, et al., "Receptor-like function of heparin in the binding and uptate of neutal lipids," *Proc. Natl. Acad. Sci. USA* 85:7438–7442 (1988).

Bremel, R.D., Yom, H.C. and Bleck, G.T., "Alteration of Milk Composition Using Molecular Genetics," *J. Dairy Sci.* 72:2826–2833 (1989)*.

Brodt–Eppley and Hui, "Dietary regulation of cholesterol esterase mRNA level in rat pancreas," *J. of Lipid Res.* 35:27 (1994).

Brown, M.S., and J.L. Goldstein, "The Hyperlipoproteinemias and Other Disorders of Lipid Metabolism," in *Harrison's Principles of Internal Medicine* 1650–1661.

Clare, J.J. et al., "High–Level Expression of Tetanus Toxin Fragment in *Pichia pastoris* Strains Containing Multiple Tanden Integrations of the Gene," *Bio/Technology* 9:455–460 (1991).

Clark, et al., "Inhibition of Hypercholesterolemia (Hyper C) By Specific Pancreatic Cholesterol Ester Hydrolase (PCEH) Inhibitors," *FASEB J.* 6"PA1388 (1992).

Cullen, D. et al., "Controlled Expression and Secretion of Bovine Chymosin in *Aspergillus nidulans*," *Bio/Technology* 5:369–378 (1987).

Cullen, D., Gray, G.L., and Berka, R.M., "Molecular Cloning Vectors for Aspergillus and Neurospora,"n *A Survey of Molecular Cloning Vectors and their Uses*, (Butterworth Publishers, Stoneham, MA (1986)*.

DiPersio, et al., "Purification of Pancreatic Cholesterol Esterase Expressed in Recombinant Baculovirus–Infected Sf9 Cells," *Protein Expr. Purif.* 3:114–120 (1992).

Downs, D. et al., "Proline-rich domain and glycosylation are not essential for the enzymic activity of bile salt–activated lipase. Kinae studies of a truncated form of the enzyme (T–BAL) expressed in *E. coil*," *Biochemistry* 33:7980–7985 (1994).

Dubois, et al., "Colorimetric Method for Determination of Sugars and Related Substances," *Anal. Chem.* 28:350–356 (1956).

Elhammer, A.P. et al., "The Specificity of UDP–GalNAc: Polypeptide N–Acetylgalactosaminyltransferase as Inferred from a Database of in Vivo Substrates and from the in Vitro Glycosylation of Proteins and Peptides," *J. Biol. Chem.* 268:10029–10038 (1993).

(List continued on next page.)

*Primary Examiner*—Herbert J. Lilling
*Attorney, Agent, or Firm*—Arnall Golden & Gregory, LLP

[57] ABSTRACT

Compositions derived from all or a portion of the carboxy terminal region of human bile salt-activated lipase (BAL) are described, which, when orally ingested, compete with native BAL in binding to the intestinal surface, thus reducing the physiological role of BAL in mediating the transfer of cholesterol into the intestinal cells, and, as a result, reducing the amount of cholesterol absorbed from the intestine into the blood stream. Useful derivatives of the carboxy terminal region of BAL are derived from all or portion of the region containing amino acid residues 539 to 722, and have a mucin-like structure containing at least three of the repeating proline-rich units of eleven amino acid residues each.

9 Claims, 5 Drawing Sheets

OTHER PUBLICATIONS

Freed, et al., "Bile salt-stimulated lipase in non-primate milk: longitudinal variation and lipase characteristics in cat and dog milk," *Biochim. and Biophy. Acta* 878:209–215 (1986).

Gallo, et al., "Inhibition of Cholesterol Absorption in Rat Intestine with a Specific Cholesterol Esterase Inhibitor," *FASEB Journal* 6(4): PA1388 (1992).

Ganong, W.F., *Review of Medical Physiology* 249–250 (Lange Medical Publications, 1985)*.

Gray, et al., "Primary structure of *Mucor miehei* aspartyl protease: evidence for a zymogen intermediate," *Gene* 48:41–53 (1987).

Griggs, et al., "Identification and Quantitation of Alditol Acetates of Neutral and Areinc Sugars from Mucins by Automated Gas–Liquid Chromatography," *Anal. Biochem.* 43:369–381 (1971).

Hall and Muller, "Studies on the Bile Salt Stimulated Lipolytic Activity of Human Milk Using Whole Milk as Source of Both Substrate and Enzyme," *Pediatr. Res.* 16:251–255 (1982).

Hernell and Blackberg, "Bile-Salt-Stimulated Lipase of Human Milk and Lipid Digestion in the Neonatal Period," *J. Pediatr. Gastro. and Nutri.* 2(Suppl. 1):S242–S247 (1983).

Hewick, R.M., et al., "A Gas–Liquid Solid Phase Peptide and Protein Sequenator," *J. Biol. Chem.* 256:7990–7997 (1981).

Huang and Hui, "Metabolic fate of pancrease–derived cholesterol esterase in intestine: an in vitro study using Caco-2 cells," *J. of Lipid Res.* 31:2029 (1990).

Hui, D.Y., and J.A. Kissel, "Sequence identify between human pancreatic cholesterol esterase and bile salt-stimulated milk lipase," *FEBS Lett.* 276:131–134 (1990).

Innis, M.A., and D.H. Gelfand, "Optimization of PCRs," *PCR Protocols. A Guide to Methods and Application* 3–12, Innis, M.A., et al. (Eds.), Academic Press, New York, N.Y. (1990)*.

Jaenisch, R., "Transgenic Animals," *Science* 240:1468–1474 (1988).

Klag, M.J., et al., "Serum Cholesterol in Young Men and Subsequent Cardiovascular Disease," *New Eng. Med.*, 328(5), pp.313–318 (Feb. 4 1993).

Kraft, et al., "Using Mini-Prep Plasmid DNA for Sequencing Double Stranded Templates with Sequenase," *BioTechniques* 6:544–547 (1988).

Leary, W.E., "Survey Finds Major Gains in Cutting Blood Cholesterol," *New York Times*, section A, p. 18, col. 3 (Jun. 16, 1993).

Lopez-Candales, et al., "Cholesterol Transport Function of Pancreatic Cholesterol Esterase: Directed Sterol Uptake and Esterification in Enterocytes," *Biochem.* 32:12085–12089 (1993).

Lowry, O.H., et al., "Protein Measurement with the Folin Phenol Reagent," *J. Biol. Chem.* 193:265 (1951).

Luckow, V.A. and Summers, M.D., "Trends in the Development of Baculovirus Expression Vectors", *Bio/Technology* 6:47 (1988).

McKean, et al., "Effects of Inhibitors of Pancreatic Cholesterol Ester Hydrolase (PCEH) On $^{14}$C–cholesterol Absorption in Animal Models," *FASEB Journal* 6(4):PA1388 (1992).

Nilsson, J., et al., "cDNA cloning of human–milk bile-salt-stimulated lipase and evidence for its identity to pancreatic carboxylic ester hydrolase," *Eur. J. Biochem.* 192:543–550 (1990).

Nilsson–Ehle, P., and M.C. Schotz, "A stable, radioactive substrate emulsion for assay of lipoprotein lipase," *J. Lipid Res.* 17:536–541 (1976)*.

Poorman, et al., "Isolation and Characterization of Native Human Renin Derived from Chinese Hamster Ovary Cells," *Proteins* 1:139–145 (1986).

Reue, K., et al., "cDNA cloning of carboxyl ester lipase from human pancreas reveals a unique proline–rich repeat unit," *J. Lipid Res.* 32:267–276 (1991).

Rudd, Edwin A., "Pancreatic carboxyl ester," *Lipases* (Elsevier, publishers, 1984).

Scahill, S.J., et al., "Expression and characterization of the product of a human immune interferon cDNA gene in Chinese hamster ovary cells," *Proc. Natl. Acad. Sci., U.S.A* 80:4654–4658 (1983).

Segel, I.H., "Enzyme Activation," *Enzyme Kinetics* 227–231, John Wiley & Sons, New York (1975).

Studier, F.W., et al., "Use of T7 RNA Polymerase to Direct Expression of Cloned Genes," *Methods Enzymol.* 185:60–89 (1990).

Wang, et al., "Kinetics of Acylglycerol Sequential Hydrolysis by Human Milk Bile Salt Activated Lipase and Effect of Taurocholate as Fatty Acid Acceptor," *Biochem.* 27:4834 (1988).

Wang & Kloer, "Kinetic Properties of Human Pancreatic Carboxylesterase," *Biochim. et Biophys. Acta* 754:142–149 (1983).

Wang, C.–S. and J.A. Hartsuck, "Bile salt–activated lipase. A multiple function lipolytic enzyme," *Biochim. Biophys. Acta* 1166:1–19 (1993).

Wang and Johnson, "Purification of Human Milk Bile Salt-Activated Lipase," *Anal. Biochem.* 133:457–461 (1983).

Wang, C.–S., "Human Milk Bile Salt–activated Lipase," *J. Biol. Chem.* 256:10198–10202 (1981).

Wang, "Acyl–chain specificity of human milk bile–salt–activated lipase," *Biochem. J.* 279:297–302 (1991).

Wang, C.–S., and R.L. Smith, "Lowry Determination of Protein in the Presence of Triton X–100," *Anal. Biochem.* 63:414–417 (1975).

Wang, et al., "Bile Salt–Activated Lipase Mediates Cholesterol Absorption by Binding of its Mucin–Like Region to Intestinal Surface," *Science* (1995)*.

Wang, et al., "Bile–salt–activated lipase: effect on kitten growth rate," *Am. J. Clin. Nutr.* 49:457–463 (1989).

Wang, "Purification of Carboxyl Ester Lipase from Human Pancrease and the Amino Acid Sequence of the N–Terminal Region," *Biochem. and Biophys. Res. Comm.* 155:950 (1988).

Westphal, H., "Transgenic mammals and biotechnology," *FASEB J.* 3:117–120 (1989).

"CV Therapeutics Begins Phase I Trial on Cholesterol–Reduction Agent," *Biotech. Bulletin* p. 11 (1994).

1

METHOD AND COMPOSITIONS FOR REDUCING CHOLESTEROL ABSORPTION

BACKGROUND OF THE INVENTION

This application is a continuation-in-part of U.S. Ser. No. 08/347,718, filed Dec. 1, 1994.

The present invention is in the field of dietary science and more particularly relates to the use of bile salt-activated lipase to reduce cholesterol uptake in the intestine.

The U.S. government has certain rights in this invention by virtue of research grant HD-23472 from the National Institutes of Health.

Cardiovascular and Other Diseases Associated with High Cholesterol.

Hyperlipidemias, particularly hypercholesterolemia and the hyperlipoproteinemias, are among the most potent risk factors in the causation of atherosclerosis. Hyperlipoproteinemias are also implicated in the development of pancreatitis. A long-established theory suggests that the higher the circulating levels of cholesterol, usually in the form of low density lipoproteins (LDLs) containing cholesterol, the more likely it is to gain entrance to the arterial wall and cause atherosclerosis. (Brown and Goldstein, "The Hyperlipoproteinemias and Other Disorders of Lipid Metabolism," in *Harrison's Principles of Internal Medicine* 1650–1661 (Braunwald et al., 1987)).

Cardiovascular disease is the leading cause of death in women and middle-aged American men. In 1988, more than 41,000 U.S. residents died of cardiovascular disease before the age of 50. Atherosclerosis, however, which is known to contribute to cardiovascular disease and stroke, begins at a much earlier age. Fatty streaks are common in the arterial walls of children, and a high prevalence of coronary-artery lesions has been found in young men who die accidentally or violently. Children and adolescents with elevated serum cholesterol levels are more likely than their counterparts with normal cholesterol levels to have parents with coronary heart disease. Higher serum cholesterol levels in childhood have been associated with aortic atherosclerosis at autopsy in adolescents and young adults, and both aortic and coronary atherosclerosis in men ranging from 15 to 34 years of age have been correlated with postmortem cholesterol levels (Klag et al., *New Eng. J. Med.* 328(5):313–318 (Feb. 4, 1993)).

Cholesterol is used by the body in the synthesis of the steroid hormones by certain endocrine glands and of bile acids by hepatocytes, and is an essential constituent of cell membranes. It is found only in animals. Related sterols occur in plants, but plant sterols are not absorbed from the gastrointestinal tract. Most of the dietary cholesterol is contained in egg yolks and animal fat.

Cholesterol that is taken up in the intestine is derived directly from the diet and from cholesterol-containing bile salt and acids and free cholesterol synthesized in the liver and secreted into the intestine via bile ducts. Cholesterol esters from the bile and diet are absorbed from the lumen of the small intestine by the intestinal epithelial lining cells and incorporated intracellularly into chylomicrons and, in minor amounts, incorporated into very low density lipoproteins (VLDLs), both of which are secreted into lymphatics that ultimately join the bloodstream. The chylomicrons and VLDLs deliver their triacyglycerols and some of their cholesterol to cells in endothelial, muscle, and adipose tissue. The cholesterol-enriched chylomicron remnants and VLDLs then deliver cholesterol back to the hepatocytes and to other cells of the vascular wall along the way (Ganong, *Review of Medical Physiology* 249–250 (Lange Medical Publications, 1985). The VLDLs from intestinal and liver cells can be converted to low density lipoproteins (LDLs) by discharge of their triacylglycdrols. LDLs contain three-fourths of the total plasma cholesterol.

In hypercholesterolemia, the increase in the blood cholesterol level is associated mainly with a rise in LDL concentrations. However, the specific causes of hypercholesterolemia are complicated and varied. At least one kind of hypercholesterolemia is caused by a mutation in the gene for the LDL receptor that moves cholesterol out of the blood, primarily in the liver. Much more commonly, hypercholesterolemia has been associated with high dietary cholesterol, resulting in high cholesterol uptake from the intestine into the circulating blood.

Reduction of hypercholesterolemia results in a delayed onset of atherosclerosis and a decrease in progression of atherosclerosis, thus reducing the risk of coronary heart disease in humans and other primates. Specifically, there is evidence in animals, most notably primates, that relatively complicated plaques induced by hyperlipidemia will regress, and that further progression of atherosclerosis will cease when hyperlipidemia is removed. Therefore, efforts to prevent atherogenesis, to interrupt progression, and perhaps to promote regression of existing lesions by risk factor reduction are warranted (Bierman, "Disorders of the Vascular System: Atherosclerosis and Other Forms of Arteriosclerosis," in *Harrison's Principles of Internal Medicine* 1014–1024, (Braunwald et al., 1987)).

Some forms of hyperlipidemia, including hypercholesterolemia, are potentially partially reversible with current techniques of preventive management. However, none of the current techniques is completely successful and many are associated with unwanted side effects and complications. Taking cholesterol-lowering drugs can result in a twenty percent reduction in serum cholesterol. However, drugs are not always warranted for hypercholesterolemia, and some of the hypolipemic drugs, such as Lovastatin, mevastatin, cholestyramine (Questran), Clofibrate, Probucol, and nicotinic acid, may have serious side effects, including an increase in mortality through liver complications, or less severe side effects, such as constipation (cholestyramine), skin flushes, and muscle dysfunction or may have an effect in lowering blood triacylglycerol but not cholesterol. Dietary therapy is usually recommended for all patients with hypercholesterolemia but is not always effective.

Accordingly, there is a need for methods and compositions which are effective in lowering blood lipid levels, especially cholesterol levels, especially those that do not in themselves have significant side effects, and in treating disease states associated with high levels of blood lipids, especially in those persons at high risk of heart disease, or who have already suffered heart attacks.

It is therefore an object of the present invention to provide compositions and methods of use in lowering serum cholesterol in a patient in need thereof.

SUMMARY OF THE INVENTION

Compositions derived from all or a portion of the carboxy terminal region of human bile salt-activated lipase (BAL) are described, which, when orally ingested, compete with native BAL in binding to the intestinal surface, thus reducing the physiological role of BAL in mediating the transfer of cholesterol into the intestinal cells, and, as a result, reducing the amount of cholesterol absorbed from the intestine into the blood stream. Useful derivatives of the carboxy terminal region of BAL are derived from all or portion of the region containing amino acid residues 539 to 722, and have a mucin-like structure containing at least three of the repeating proline-rich units of eleven amino acid residues each. Preferred proline-rich units have the consensus sequence PVPPTGDSGAP (Sequence ID No. 6).

DETAILED DESCRIPTION OF THE INVENTION

Compositions including all or a portion of the carboxy terminal region of bile salt-activated lipase (BAL), or functional equivalents thereof, are described, which, in the intestine, compete with native BAL in binding to the intestinal surface to reduce the function of endogenous BAL to mediate the uptake of cholesterol eaters or free cholesterol in the form of free cholesterol taken into the blood stream.

Bile Salt-activated Lipase.

Warm-blooded animals synthesize many forms of lipases of different structures and activities, which are secreted by mammary gland cells and by cells in several of the digestive organs, including the pancreas, stomach, and small intestine. Bile salt-activated lipase (BAL), which is virtually inactive by itself toward physiological substrates, is activated in the intestine by bile salts. BALs are synthesized and secreted by the pancreas and also by the mammary glands of only few species, including humans, gorillas, cats, and dogs. The amino acid and cDNA sequences of human milk BAL are the same as those of pancreatic BAL, also known as pancreatic carboxylesterase, and closely related to or the same as lipases referred to in the literature as lysophospholipase, cholesterol esterase, sterol ester hydrolase, non-specific lipase, lipase A, carboxyl ester lipase, and cholesterol ester hydrolase, with certain species differences, primarily with respect to the number of repeating units in the carboxy region (Wang and Hartsuck, *Biochim. Biophys. Acta* 1166:1–19 (1993)). Pancreatic BAL is distinct from other types of non-bile salt activated lipases, such as pancreatic lipase and phospholipase.

In the intestinal lumen, BAL becomes attached to the intestinal surfaces, most likely the surface of intestinal epithelial lining cells via a specific receptor. It can be released from the lumenal surface by EGTA, galactose and fucose, but not by heparin, isotonic buffer, or sodium chloride, as demonstrated below. BAL, in the required presence of bile salts, is essential for hydrolyzing cholesterol esters to free cholesterol or to bind free cholesterol in the food. Both of these processes are necessary to allow the uptake of cholesterol since it is the only known pancreatic lipolytic enzyme that can mediate cholesterol uptake. BAL also hydrolyses carboxyl ester bonds of acylglycerols, phospholipid, and vitamin esters, forming fatty acids and glycerol, and can act on emulsified, micellar, or soluble substrates. It is thought that bile salt causes conformational change in BAL to provide active site access for the bulky substrate molecule and provides additional lipid binding capability in forming the enzyme-substrate complex. Additionally, it is thought that bile salt acts as a fatty acid acceptor during BAL catalysis.

Figure 1:
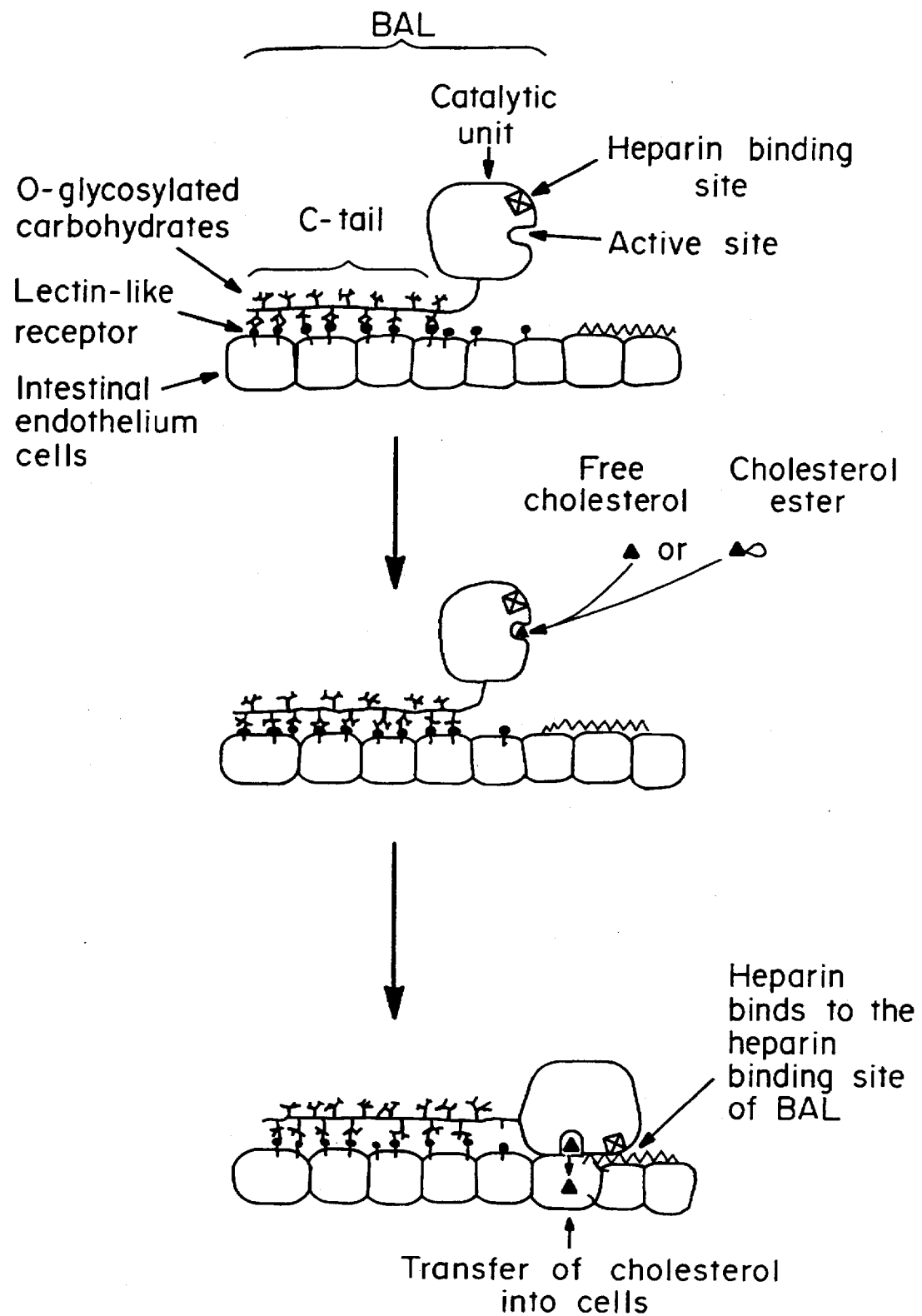
FIG. 1 shows the proposed binding of BAL to intestinal endothelium cells via the C-tail O-glycosylated carbohydrate binding to a lectin-like receptor, binding of cholesterol and cholesterol ester to BAL, hydrolyzing cholesterol ester by BAL, followed by transfer of enzyme bound cholesterol into cells.

The proposed mechanism for the action of BAL is shown in FIG. 1. BAL binds via the C-tail O-glycosylated carbohydrates to a lectin-like receptor on the surface of intestinal endothelium cells. The catalytic unit of the enzyme remains away from the endothelium cells, with the heparin binding site and active site exposed. Free cholesterol or cholesterol ester is then bound to the active site, and, in the case of cholesterol ester, it is hydrolyzed to free cholesterol. The catalytic unit then binds to the heparin on the cell surface and transfers the cholesterol into the cells.

Cholesterol, fatty acids, and monoacyglycerols derived from lipolysis by BAL in the intestinal lumen are taken up by the intestinal epithelial lining cell (mucosal cell), where these are reesterified to intracellular triacylglycerols. Cholesterol interacts in the cell with these reesterified triacylglycerols plus apolipoproteins and phospholipid to form chylomicrons and very low density lipoproteins, which are secreted into the lymphatics that ultimately join the blood vascular system for systemic circulation.

The Carboxy Terminal Region of the BAL Molecule.

The full, mature, human BAL contains 722 amino acid residues (Sequence ID No. 1). The carboxy terminal region of BAL refers to a region in the native BAL molecule including residues 539 to 722. This carboxy terminal region of BAL, along with derivatives of this region that retain the intestinal binding activity, are referred to herein as "C-tail." The C-tail of the human BAL molecule has many O-linked oligosaccharide units which form a mucin-like structure. The amino acid sequence of the native human C-tail contains sixteen repeating proline-rich units of eleven amino acid residues each, most having the consensus sequence of PVPPTGDSGAP (Sequence ID No. 6) (Baba et al., *Biochemistry* 30:500–510 (1991)). By performing the beta-elimination reaction, the native C-tail was determined to be O-glycosylated primarily at threonine and, to a small degree, if any, at one serine residue. It is believed that the serine residue, which has an adjacent aspartic acid, is not favorable for the O-glycosylation (Elhammer et al., *J. Biol. Chem.* 268:10029–10038 (1993)). A peptide prepared by cyanogen bromide digestion of the C-tail was found to contain most of the carbohydrate of the native BAL (Baba et al. (1991)).

As demonstrated below, truncated versions of BAL which lack the C-tail binding portion, referred to herein as "T-BAL," are ineffective in transferring cholesterol into intestinal cells since the enzyme is not bound to the intestinal surface. Similarly, C-tail alone can bind to the intestinal surface, and in fact, can compete with native BAL for this binding, but cannot transfer cholesterol since the catalytic unit is either not functional or not present.

C-tail proteins.

Derivatives of the carboxy terminal region of BAL, derived from all or portion of the region containing amino acid residues 539 to 722, and having a mucin-like structure containing at least three of the repeating proline-rich units of eleven amino acid residues each, is referred to herein as C-tail. As used herein, a proline-rich unit refers to any of the repeated eleven amino acid groups present in any naturally occurring form of BAL, or derivatives thereof which, when combined with two or more other proline-rich units, results in a protein which binds to intestinal endothelium cells and/or inhibits the binding of native BAL. Preferred proline-rich units have the consensus sequence PVPPTGDSGAP (Sequence ID No. 6). As used herein, a "C-tail protein" refers to any protein containing three or more proline-rich units as defined above, which binds to intestinal endothelium cells and/or inhibits the binding of native BAL. This can be achieved, for example, through the use of BAL consisting of all or part of the mucin-like C-tail region of native BAL. Native BAL is a form of C-tail protein.

A C-tail protein should include at least three of the repeating proline-rich units of eleven amino acid residues each. The rat pancreatic esterase C-tail which has only four repeating units still binds to rat intestine surface. Preferred C-tail proteins have at least 10, and most preferably at least 16, proline-rich units. It is expected that C-tail proteins with fewer proline-rich units will bind to intestinal surface with a lower affinity. The binding affinity of any C-tail protein can be increased by using proline-rich units that most closely match the consensus sequence (Sequence ID No. 2). C-tail proteins can be constructed by combining three or more proline-rich units, where the proline-rich units have the native amino acid sequence of a proline-rich unit from any BAL, have the consensus amino acid sequence of the human proline-rich unit, or derivatives of these amino acid sequences, such that the C-tail protein retains the ability to bind to intestinal endothelium cells and/or inhibit the binding of native BAL.

Amino acid sequence variants.

The C-tail protein may be O-glycosylated to different extents with respect to the number of threonine and serine residues, and can include amino acid deletions, substitutions, or additions which do not significantly impair binding to the intestinal surface. The substitutions, deletions, or additions to C-tail proteins, which do not alter binding are readily determined by a screening assay, in which the protein is allowed to bind to intestinal surface, then removed by washing with buffer with increasing concentrations of salt. An example of a BAL which contains a deletion not affecting binding of the C-tail is a BAL lacking the heparin binding site, which is postulated to be present between amino acid residues 56 and 62 (Baba et al. (1991)).

Amino acid sequence variants of C-tail protein fall into one or more of three classes: substitutional, insertional or deletional variants. Insertions include amino and/or carboxyl terminal fusions as well as intrasequence insertions of single or multiple amino acid residues. Fusions include hybrids of mature BAL and the C-tail protein with polypeptides that are homologous with BAL, for example, in the case of human BAL, secretory leaders from other secreted human proteins. Fusions also include hybrids of BAL and the C-tail protein with polypeptides homologous to the host cell but not to BAL, as well as, polypeptides heterologous to both the host cell and BAL. Preferred fusions are amino terminal fusions with either prokaryotic peptides or signal peptides of prokaryotic, yeast, viral or host cell signal sequences. It is not essential that the signal sequence be devoid of any residual mature sequence from the protein whose secretion it ordinarily directs but this is preferable in order to avoid the secretion of a C-tail protein fusion.

Insertions can also be introduced within the coding sequence of the proline-rich unit repeat region of the C-tail protein. Such insertions can include the addition of unrelated amino acids or the insertion of one or more additional proline-rich units. In the context of inserted amino acids, "unrelated" amino acids refer to amino acid sequences that are unrelated to the sequence of the proline-rich units of BAL. In the case of proline-rich units, the inserted units can be heterologous units from non-human BAL, units having the consensus sequence (Sequence ID No. 6), or additional repeats of individual human proline-rich units. In the case of insertion of unrelated amino acids, however, the insertion will ordinarily consist of smaller insertions than those of amino or carboxyl terminal fusions, or than those of proline-rich units, on the order of 1 to 4 residues.

Insertional amino acid sequence variants of C-tail proteins are those in which one or more amino acid residues are introduced into a predetermined site in the target C-tail protein. Most commonly, insertional variants are fusions of heterologous proteins or polypeptides to the amino or carboxyl terminus of the C-tail protein. Preferably, these heterologous polypeptides are heterologous forms of the proline-rich units present in human BAL. Immunogenic C-tail protein derivatives are made by fusing a polypeptide sufficiently large to confer immunogenicity to the target sequence by cross-linking in vitro or by recombinant cell culture transformed with DNA encoding the fusion. Such immunogenic polypeptides can be bacterial polypeptides such as trpLE, beta-galactosidase and the like.

Deletions are characterized by the removal of one or more amino acid residues from the C-tail protein sequence. It is preferred that deletions involve deletions of entire proline-rich units. If individual amino acids within the proline-rich units are deleted, no more than about from 2 to 6 residues are deleted at any one site within the C-tail protein molecule.

These variants ordinarily are prepared by site specific mutagenesis of nucleotides in the DNA encoding the C-tail protein, thereby producing DNA encoding the variant, and thereafter expressing the DNA in recombinant cell culture. However, variant C-tail protein fragments having up to about 100 to 150 residues may be conveniently prepared by in vitro synthesis. The variants typically exhibit the same qualitative biological activity as the naturally-occurring analogue, that is, specific intestinal binding, although variants also are selected in order to modify the characteristics of the C-tail protein as will be more fully described below.

While the site for introducing an amino acid sequence variation is predetermined, the mutation per se need not be predetermined. For example, in order to optimize the performance of a mutation at a given site, random mutagenesis may be conducted at the target codon or region and the expressed C-tail protein variants screened for the optimal combination of desired properties. Techniques for making substitution mutations at predetermined sites in DNA having a known sequence are well known, for example M13 primer mutagenesis.

Amino acid substitutions are typically of single residues; insertions usually will be on the order of about from 1 to 10 amino acid residues, or entire proline-rich units; and deletions will range about from 1 to 30 residues, or entire proline-rich units. Deletions or insertions preferably are made in adjacent pairs, that is a deletion of 2 residues or insertion of 2 residues. Substitutions, deletions, insertions or any combination thereof may be combined to arrive at a final construct. Obviously, the mutations that will be made in the DNA encoding the variant BAL or C-tail protein must not place the sequence out of reading frame and preferably will not create complementary regions that could produce secondary mRNA structure (EP 75,444A).

Substitutional variants are those in which at least one residue in the C-tail protein has been removed and a different residue inserted in its place. Such substitutions generally are made in accordance with the following Table I when it is desired to finely modulate the characteristics of C-tail protein or BAL.

TABLE I

| Original Residue | Exemplary Substitutions |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table I, that is, selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in BAL or C-tail protein properties will be those in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histidyl, is substituted for (or by) an electronegative residue, for example, glutamyl or aspartyl; or (d) a residue having a bulky side chain, for example, phenylalanine, is substituted for (or by) one not having a side chain, for example, glycine.

Substitutional or deletional mutagenesis can be employed to eliminate N- or O-linked glycosylation sites (for example by deletion or substitution of asparaginyl residues in Asn-X-Thr glycosylation sites), improve expression of BAL or C-tail protein or alter the half life of the protein. Alternatively, unglycosylated BAL or C-tail protein can be produced in recombinant prokaryotic cell culture. Such unglycosylated forms are expected to lack, or have reduced, intestinal binding activity. Deletions of cysteine or other labile residues also may be desirable, for example in increasing the oxidative stability or selecting the preferred disulfide bond arrangement of BAL. Deletions or substitutions of potential proteolysis sites, for example, Arg, is accomplished for example by deleting one of the basic residues or substituting one by glutaminyl or histidyl residues.

Full length BAL which has an inactivated catalytic site can also be used for competitive inhibition of binding of cholesterol. Since the catalytic site is inactivated, the BAL cannot facilitate uptake of cholesterol. The catalytic site can be inactivated by amino acid deletion or substitution in the active site of the recombinant BAL. The catalytic site can also be inactivated by chemical modification of BAL at or near the active site, for example, by proteolysis or other enzymic reactions, by binding of an irreversible enzyme inhibitor to the catalytic site, or by means which disrupt the three dimensional conformation of the catalytic unit of BAL (since the binding of the C-tail to intestine is not dependent on its conformation). Examples of disruptive means include detergents and heat.

Useful BAL derivatives that do not hydrolyze cholesterol esters or bind heparin include polypeptides that may or may not be substantially homologous with BAL. These BAL derivatives are produced by the recombinant or organic synthetic preparation of BAL fragments or by introducing amino acid sequence variations into intact BAL so that it no longer demonstrates cholesterol ester hydrolysis and/or heparin binding activity as defined above.

BAL derivatives that do not hydrolyze cholesterol esters or bind heparin as described above are useful as immunogens for raising antibodies to active BAL. Such BAL derivatives, referred to as "BAL protein antagonists" may be used to neutralize the cholesterol uptake-mediating activity or BAL. Such a BAL protein antagonist may bind to the intestinal lining thereby blocking binding of native BAL. BAL protein antagonists are useful in the therapy of various cholesterol disorders for example, hypercholesterolemia, especially hypercholesterolemia exacerbated by dietary cholesterol intake.

BAL, BAL derivatives, and C-tail protein molecules may also be covalently modified. Such modifications are made by reacting targeted amino acid residues of the recovered or synthesized protein with an organic derivatizing agent that is capable of reacting with selected side chains or terminal residues. Alternately, post-translational modification in selected recombinant host cells may be used to modify the protein. The resulting covalent derivatives are useful as immunogens or to identify residues important for biological activity as well as for altering pharmacological characteristics of the molecule, such as half life, binding affinity and the like, as would be known to the ordinarily skilled artisan.

Certain post-translational derivatizations are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be used.

Other post-translational modifications include hydroxylation of proline and lysine, phosphorylation of hydroxyl groups of seryl or threonyl residues, methylation of the o-amino groups of lysine, arginine, and histidine side chains (Creighton, Proteins: *Structure and Molecular Properties* pages 79–86 (W. H. Freeman & Co., San Francisco, 1983)), acetylation of the N-terminal amine and, in some instances, amidation of the C-terminal carboxyl.

Production of C-tail proteins.

There are several ways to produce a C-tail protein. For example, one may obtain natural or recombinant BAL and cleave off the native C-tail using proteases, such as trypsin, chymotrypsin, pepsin and others, or chemical methods such as cyanogen bromide cleavage at Met-X bonds. Alternatively, one can express in an eukaryotic host the gene or cDNA encoding the sequence including the C-tail region of BAL, or any C-tail protein as described above, either by itself or as fusion to other non-BAL DNA sequences which may facilitate either the expression or the purification of recombinant C-tail protein. Recombinant BAL or C-tail protein fusions can be subjected to cleavages and purification to obtain purified C-tail.

BAL can be purified from natural sources, such as the milk of human and certain species or animal intestines or pancreatic juice, although this is impractical on a large scale. It is preferably produced by genetic engineering using standard recombinant DNA technology and eukaryotic host cells, such as yeast or cultured mammalian or insect cells, so the C-tail can be properly glycosylated, or in the milk of transgenic non-human animals.

One method of isolating BAL from milk is described by Wang and Johnson, *Anal. Biochem.* 133:457–461 (1983), incorporated herein by reference. "Essentially free from" or "essentially pure," when used to describe the state of BAL or C-tail protein produced as described herein, means free of protein or other materials normally associated with BAL in its in vivo physiological milieu as for example when BAL is obtained from blood and/or tissues by extraction and purification. Other materials include infectious organisms such as, for example, the causative agent of acquired deficiency syndrome (AIDS). BAL and C-tail protein produced by the method of the instant invention is greater than or equal to 95% purity.

To synthesize recombinant BAL or C-tail protein, one may utilize the cDNA sequence (Sequence ID No. 3) encoding human milk bile salt activated lipase (Sequence ID No. 2) set out in U.S. Pat. No. 5,200,183 to Tang and Wang; Baba et al. (1991); or Nilsson et al., *Eur. J. Biochem.* 192:543–550 (1990), all incorporated herein by reference. This sequence can be readily adapted for expression of any C-tail protein as described above, either by deletion, addition, or substitution of the sequence encoding native BAL C-tail, as described above.

A DNA isolate is understood to mean chemically synthesized DNA, cDNA or genomic DNA with or without the 3' and/or 5' flanking regions. DNA encoding BAL can be obtained from other sources than human by a) obtaining a cDNA library from the liver, breast, pancreas, or other tissues containing BAL mRNA of the particular animal, b) conducting hybridization analysis with labelled DNA encoding human BAL or fragments thereof (usually, greater than 100 bp) in order to detect clones in the cDNA library containing homologous sequences, and c) analyzing the clones by restriction enzyme analysis and nucleic acid sequencing to identify full-length clones. If full length clones are not present in the library, then appropriate fragments may be recovered from the various clones using nucleic acid sequence disclosed herein and ligated at restriction sites common to the clones to assemble a full-length clone encoding BAL.

"Transformation" means introducing DNA into an organism so that the DNA is replicable, either as an extrachromosomal element or by chromosomal integration. Unless indicated otherwise, the method used herein for transformation of the host cells is the method of Graham and van der Eb, *Virology* 52:456–457 (1973). However, other methods for introducing DNA into cells such as by nuclear injection or by protoplast fusion may also be used. If prokaryotic cells or cells which contain substantial cell wall constructions are used, the preferred method of transfection is calcium treatment using calcium chloride as described by Cohen et al., *Proc. Natl. Acad. Sci. USA* 69:2110 (1972).

Construction of suitable vectors containing the desired coding and control sequences employ standard ligation techniques. Isolated plasmids or DNA fragments are cleaved, tailored, and relegated in the form desired to form the plasmids required.

Since glycosylation of the C-tail is essential, prokaryotic cells are not useful as expression hosts for C-tail which binds to receptor. However, in general, prokaryotes are used for cloning of DNA sequences in constructing the vectors useful for expression. For example, *E. coli* W3110 (F, á, prototrophic, ATTC No. 27325), bacilli such as *Bacillus subtilus*, and other enterobacteriaceae such as *Salmonella typhimurium* or *Serratia marcescans*, and various pseudomonas species can be used.

In general, plasmid vectors containing promoters and control sequences which are derived from species compatible with the host cell are used with these hosts. The vector ordinarily carries a replication site as well as one or more marker sequences which are capable of providing phenotypic selection in transformed cells. For example, *E. coli* is typically transformed using a derivative of pBR322 which is a plasmid derived from an *E. coli* species (Boliver et al., *Gene* 2:95 (1977)). pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA construction.

Promoters suitable for use with prokaryotic hosts illustratively include the β-lactamase and lactose promoter systems (Chang et al., *Nature* 275:615 (1978); and Goeddel et al., *Nature* 281:544 (1979)), alkaline phosphatase, the tryptophan (trp) promoter system (Goeddel et al., *Nucleic Acids Res.* 8:4057 (1980) and EPO Appln. Publ. No. 36,776) and hybrid promoters such as the tac promoter (de Boer et al., *Proc. Natl. Acad. Sci. USA* 80:21–25 (1983)). However, other functional bacterial promoters are suitable. Their nucleotide sequences are generally known, thereby enabling a skilled worker operably to ligate them to DNA encoding BAL or C-tail protein using linkers or adaptors to supply any required restriction sites (Siebenlist et al., *Cell* 20:269 (1980)). Promoters for use in bacterial systems also will contain a Shine-Dalgarno (S.D.) sequence operably linked to the DNA encoding BAL or C-tail protein.

For analysis to confirm correct sequences in plasmids constructed, the ligation mixtures are used to transform *E. coli* K12 strain 294 (ATCC 31446) and successful transformants selected by ampicillin or tetracycline resistance where appropriate. Plasmids from the transformants are prepared, analyzed by restriction and/or sequenced by the method of Messing et al., *Nucleic Acids Res.* 9:309 (1981) or by the method of Maxam et al., *Methods in Enzymology* 65:499 (1980).

Host cells can be transformed with the expression vectors and cultured in conventional nutrient media modified as is appropriate for inducing promoters, selecting transformants or amplifying genes. The culture conditions, such as temperature and pH, are those previously used with the host cell selected for expression, and will be apparent to the ordinarily skilled artisan.

"Transfection" refers to the taking up of an expression vector by a host cell whether or not any coding sequences are in fact expressed. Numerous methods of transfection are known to the ordinarily skilled artisan, for example, CAPO$_4$ and electroporation. Successful transfection is generally recognized when any indication of the operation of this vector occurs within the host cell.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally (Lawn et al., *Nucleic Acids Res.* 9:6103–6114 (1981), and Goeddel et al. (1980)).

"Dephosphorylation" refers to the removal of the terminal 5' phosphates by treatment with bacterial alkaline phosphatase (BAP). This procedure prevents the two restriction cleaved ends of a DNA fragment from "circularizing" or forming a closed loop that would impede insertion of another DNA fragment at the restriction site. Procedures and reagents for dephosphorylation are conventional (Maniatis et al., *Molecular Cloning*, 133–134 (Cold Spring Harbor, 1982). Reactions using BAP are carried out in 50 mM Tris at 68° C. to suppress the activity of any exonucleases which may be present in the enzyme preparations. Reactions are run for 1 hour. Following the reaction the DNA fragment is gel purified.

"Ligation" refers to the process of forming phosphodiester bonds between two double stranded nucleic acid fragments (Maniatis et al., Id. at 146). Unless otherwise provided, ligation may be accomplished using known buffers and conditions with 10 units of T4 DNA ligase ("ligase") per 0.5 μg of approximately equimolar amounts of the DNA fragments to be ligated.

"Filling" or "blunting" refers to the procedures by which the single stranded end in the cohesive terminus of a restriction enzyme-cleared nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2 to 15 μg of the target DNA in 10 mM MgCl$_2$, 1 mM dithiothreitol, 50 mM NaCl, 10 mM Tris (pH 7.5) buffer at about 37° C. in the presence of a 8 units of the Klenow fragment of DNA polymerase I and 250 μM of each of the four deoxynucleoside triphosphates. The incubation generally is terminated after 30 minutes by phenol and chloroform extraction and ethanol precipitation.

Many of the above procedures for mutating, manipulating, and recombining nucleic acid molecules can also be found in the standard laboratory manual by Sambrook et al., *Molecular Cloning: A Laboratory Manual* (Cold Spring Harbor, 1989).

Since in many eukaryotic expression systems exons are excised correctly, both human BAL cDNA and human BAL genomic DNA can be used to direct the synthesis of recombinant human BAL protein(s) in native or modified forms. Human BAL gene(s) are expected to contain in their untranslated region sequences which regulate the expression of the enzyme. These regulatory sequences may even be directly used in transgenic animal expression.

Recombinant BAL protein can be produced from human BAL cDNA or genes by many different methods. These include the expression of BAL in hosts such as *E. coli*, Bacillus, yeast, fungi, insect cells, mammalian cells, and transgenic animals. Expression of T-BAL (truncated form of BAL without C-tail) in *E. coli* has been described by Downs et al., *Biochemistry* 33:7980–7985 (1994). Since prokaryotic hosts cannot excise mammalian introns from mRNA, it is preferable to express the cDNA, with appropriate modifications, in procaryotic systems, rather than the gene. However, since prokaryotes cannot glycosylate BAL, it is preferable to use eukaryotic systems for expression of BAL. When eukaryotic cells are used as hosts, either human BAL genes or cDNA can be used to direct the synthesis of the enzyme. There can also be glycosylation on BAL provided that a 'leader' or 'signal' sequence is present to direct newly synthesized BAL to the inside of the rough endoplasmic reticulum. This is important for the C-tail to reduce cholesterol uptake since the interaction of intestinal surface is through the oligosaccharides on the C-tail.

In all cases, the human BAL cDNA or gene can be inserted into appropriate expression vectors containing expression regulatory elements, such as transcription initiation signals, translation initiation signals, starting codon, termination codon, transcription terminating signals, polyadenylation signals, and others. Suitable vectors are commercially available from a variety of companies. After the recombinant vectors containing BAL cDNA or gene is transfected into the host cells, they may remain as extrachromosomal DNA or they may be integrated into the host genome. In either case, they may direct the synthesis of recombinant BAL in the host cells. Some examples for the expression of heterologous genes are described in *Methods in Enzymology*, Vol. 153, Chapters 23 to 34 (Editors, Wu and Grossman, Academic Press, 1987). Large scale culture of the BAL synthesizing host cells and the purification of the enzyme may form a cost effective commercial means of production of BAL or the C-tail. Methods are well known to those skilled in the art for the large scale production of enzymes.

Some examples of useful expression systems for the glycosylated C-tail of BAL are given below:

(1) Yeast and Fungi as host: The principles for the expression of recombinant BAL in the yeast are similar to that for *E. coli* expression. Examples are provided by Bitter et al. Methods in *Enzymology* 153:516–544 (1987). Like *E. coli*, yeast host cells may express a foreign gene either in the cytosol or, preferably in this case, as secreted protein. Unlike *E. coli* expression, the secreted expression in yeast is capable of glycosylation. There are many vectors, promoters, and leaders available for yeast expression of secretion proteins. An excellent example is the system based on the control by alcohol oxidase promoter in methylotrophic yeast, *Pichia pastoris*. Vectors pHIL-S1 and pPIC9 are commercially available (Invitrogen) and can make large quantities of secretory eukary-otic recombinant proteins (1–4 mg per L of human serum albumin, Barr et al., *Pharmaceutical Engineering* 12:48–51 (1992); 12 mg per L of tetanus toxin fragment C, Clare et al., *Bio/Technology* 9:455–460 (1991).

For expression in Saccharomyces, the plasmid YRp7, for example, (Stinchcomb et al., *Nature* 282:39 (1979); Kingsman et al., *Gene* 7:141 (1979); Techemper et al., *Gene* 10:157 (1980)) is commonly used. This plasmid already contains the trpl gene which provides a selection marker for a mutant strain of yeast lacking the ability to grow in tryptophan, for example ATCC no. 44076 or PEP4-1 (Jones, *Genetics* 85:12 (1977)). The presence of the trpl lesion as a characteristic of the yeast host cell genome then provides an effective means of selection by growth in the absence of tryptophan.

Suitable promoting sequences for use with yeast hosts include the promoters for 3-phosphoglycerata kinase (Hitzeman et al., *J. Adv. Enzyme Reg.* 7:149 (1968); and Holland, *Biochemistry* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., European Patent Publication No. 73,657A. Yeast enhancers also are advantageously used with yeast promoters.

There are small numbers of fungal expression vectors which have been successfully used to express heterologous genes. The existing fungal expression vectors integrate themselves into the host genome after transfection (Cullen et al., "Molecular Cloning Vectors for Aspergillus and Neurospora," in *A Survey of Molecular Cloning Vectors and their Uses* (Butterworth Publishers, Stoneham, Mass. 1986). When a leader is present in front of the expressed protein codons, the secreted recombinant proteins can be glycosylated. Some examples of successful expressions involve bovine chymosin (Cullen et al. *Bio/Technology* 5:369–378 (1987)) and an acid protease from a different fungus (Gray et al., *Gene* 48:41–53 (1987)).

(2) Insect cells as host: Baculovirus expression vectors for the synthesis of foreign genes in insect cells have been successfully used to express many mammalian and viral proteins as well as described for rat pancreatic BAL (DiPersio et al., *Protein Expr. Purif.* 3:114–120 (1992)). This system is capable of glycosylation and can also express recombinant proteins at a high level. The use of this system has been reviewed in some detail (Luckow and Summers, "Trends in the Development of Baculovirus Expression Vectors," *Bio/Technology*, Sep. 11, 1987). Many of vectors derived from the baculovirus expression system are now commercially available, for example, vectors pBlueBacHis A, B, C and pEBVHis A, B, C as well as the insect host cells are available through Invitrogen.

(3) Mammalian cells as host: Expression of many heterologous genes in mammalian cells has been successfully accomplished for commercial purposes. The commercial production of recombinant human tissue plasmingen activator is an example. Most of these expression vectors contains either mammalian promoter or viral promoters, polyadenylation signals, and appropriate regulatory elements for *E. coli* cloning, including antibiotic resistance genes. After the insertion of DNA encoding BAL or a C-tail protein downstream from the promoter, the vector can be first cloned in *E. coli*, isolated and transfected into mammalian cells. Neomycin or similar resistant selection markers can be either cotransfected into mammalian cells. Neomycin or similar resistant selection markers can be either cotransfected in another vector or in the same vector. For high level expression, a gene amplification system is advantageous. The transformant clones secreting BAL or C-tail protein can be identified by enzyme assays or by western blots. Successful examples of this approach with other mammalian proteins include the synthesis of glycosylated recombinant prorenin (Poorman et al., *Proteins* 1:139–145 (1986)) and human immune interferon (Scahill et al., *Proc. Natl. Acad. Sci., U.S.A* 80:4654–4658 (1983)).

Preferred promoters for controlling transcription from vectors in mammalian host cells may be obtained from various sources, for example, the genomes of viruses such as: polymoma, Simian Virus 40 (SV40), adenovirus, retroviruses, hepatitis-B virus and most preferably cytomegalovirus, or from heterologous mammalian promoters, for example, beta actin promoter. The early and late promoters of the SV40 virus are conveniently obtained as an SV40 restriction fragment which also contains the SV40 viral origin of replication (Fiers et al., *Nature* 273:113 (1978)). The immediate early promoter of the human-cytomegalovirus is conveniently obtained as a HindIII E restriction fragment (Greenaway et al., *Gene* 18:355–360

(1982)). Of course, promoters from the host cell or related species also are useful herein.

Transcription of a DNA encoding BAL or C-tail protein by higher eukaryotes is increased by inserting an enhancer sequence into the vector. Enhancers are cis-acting elements of DNA, usually from about 10 to 300 bp, that act on a promoter to increase its transcription initiation capability. Enhancers are relatively orientation and position independent having been found 5' (Laimins et al., *Proc. Natl. Acad. Sci. USA* 78:993 (1981)) and 3' (Lusky et al., *Mol. Cell Bio.* 3:1108 (1983)) to the transcription unit, within an intron (Banerji et al., *Cell* 33:729 (1983)) as well as within the coding sequence itself (Osborne et al., *Mol. Cell Bio.* 4:1293 (1984)). Many enhancer sequences are known from mammalian genes (globin, elastase, albumin, α-fetoprotein and insulin). Typically, however, one will use an enhancer from an eukaryotic cell virus. Examples include the SV40 enhancer on the late side of the replication origin (nucleotides 100 to 270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding BAL or C-tail protein. The 3' untranslated regions also include transcription termination sites.

Expression vectors may contain a selection gene, also termed a selectable marker. Examples of suitable selectable markers for mammalian cells are dihydrofolate reductase (DHFR), thymidine kinase or neomycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR cells and mouse LTK cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern and Berg, *Molec. Appl. Genet.* 1:327 (1982), mycophenolic acid, Mulligan, and Berg, *Science* 209:1422 (1980) or hygromycin, Sugden et al., *Mol. Cell. Biol.* 5:410–413 (1985). The three examples given above employ bacterial genes under eukaryotic control to convey resistance to the appropriate drug G418 or neomycin (geneticin), xgpt (mycophenolic acid) or hygromycin, respectively.

"Amplification" refers to the increase or replication of an isolated region within a cell's chromosomal DNA. Amplification is achieved using a selection agent, for example, methotraxate (MTX) which inactivates DHFR. Amplification or the making of successive copies of the DHFR gene results in greater amounts of DHFR being produced in the face of greater amounts of MTX. Amplification pressure is applied notwithstanding the presence of endogenous DHFR, by adding ever greater amounts of MTX to the media. Amplification of a desired gene can be achieved by cotransfecting a mammalian host cell with a plasmid having a DNA encoding a desired protein and the DHFR or amplification gene permitting cointegration. One ensures that the cell requires more DHFR, which requirement is met by replication of the selection gene, by selecting only for cells that can grow in the presence of ever-greater MTX concentration. So long as the gene encoding a desired heterologous protein has cointegrated with the selection gene replication of this gene gives rise to replication of the gene encoding the desired protein. The result is that increased copies of the gene, that is, an amplified gene, encoding the desired heterologous protein express more of the desired heterologous protein.

Preferred suitable host cells for expressing the disclosed vectors encoding BAL or C-tail protein in higher eukaryotes include: monkey kidney CVI line transformed by SV40 (COS-7, ATCC CRL 1651); human embryonic kidney line (293, Graham et al., *J. Gen Virol.* 36:59 (1977)); baby hamster kidney cells (BHK, ATCC CCL 10); chinese hamster ovary-cells-DHFR (CHO, Urlaub and Chasin, *Proc. Natl. Acad. Sci. USA* 77:4216 (1980)); mouse sertoli cells (TM4, Mather, *Biol. Reprod.* 23:243–251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL51); and, TRI cells (Mather et al., *Annals N.Y. Acad. Sci.* 383:44–68 (1982)).

(4) Expression of C-tail proteins or BAL in transgenic animals: Technology already exists to transfer human BAL gene into the genomes of other animals for tissue specific expression (Jaenisch, *Science* 240:1468–1474 (1988); Westphal, *FASEB J.* 3:117–120 (1989)). Some works are already in progress to alter the composition of milk by using transgenic technology (for review, see Bremel et al., *J. Dairy Sci.* 72:2826–2833 (1989)). The general approaches, as summarized in the three reviews listed above, is to construct vectors containing promoters of secretory mammary gland (milk) proteins (such as casein or milk lysozyme), DNA encoding BAL or a C-tail protein, and appropriate complementing elements. The cloned vector is then microinjected into a newly fertilized egg of cow or sheep and the egg transferred to a 'foster mother' for the fetal development and birth. The transgenic offsprings are analyzed for gene transfer by Southern blots and for the production of BAL or the C-tail protein in the milk. It is important to note that cows and sheep do not produce BAL in their milks. The transgenic animals can be interbred in order to produce a high yielding strain. The C-tail protein secreted in the milk would be fully glycosylated. Since cow and sheep do not make milk BAL, the recombinant product can be easily differentiated from the host milk proteins.

Sugar or sugar analogue containing compounds can also be synthesized by chemical reactions to mimic the C-tail structures. These can be used to bind the intestinal surface and compete with endogenous BAL in the same manner as the C-tail itself. The following examples demonstrate that galactose and fucose can elute endogenous bound BAL from rat intestinal surface, indicating that synthetic mimics of C-tail containing these sugars or their structural analogues can be used to affect the binding to intestinal surface. Since the C-tail contains repeating sequences and many glycosylation sites, the synthetic mimics can contain many sugar containing sites. The chemical linkages of sugars can be modeled based on the oligosaccharide structures of the C-tail, or the structural analogues of these oligosaccharide structures may contain essential features for effective binding to the intestinal BAL receptors. The sugars can be chemically attached to a polymer to create repeating units. Examples of suitable polymers include polypeptides, polyethylene glycol, dextran like sugar polymers and other synthetic polymers with appropriate functional groups for chemical linkage to sugars.

Pharmaceutical Applications and Compositions

As described in the examples below, it has been discovered that BAL binds through the oligosaccharides of its C-tail to lectin-like receptors on intestinal surface. This binding is an essential step in mediating cholesterol uptake by the intestine. Further, it has been discovered that the isolated C-tail of BAL can compete with BAL for binding to the receptors on the intestinal surface. It has further been shown that C-tail can competitively inhibit the intestinal uptake of cholesterol by reducing the intestinal bound BAL. The reduction of cholesterol uptake by C-tail is specific, since BAL is the only enzyme in the intestine that can mediate cholesterol uptake. BAL also hydrolyses other fatty acid esters, and therefore can facilitate the uptake of other fats. The reduction of intestinal uptake of non-cholesterol fats by C-tail, however, is not specific since other lipases in the intestine can also digest non-cholesterol fats. Accordingly, C-tail proteins, as defined above, can be administered as a therapeutic agent to individuals in need of specific reduction of cholesterol uptake, and/or more general reduction in uptake of other fats, and thereby to treat hyperlipoproteinemia, hypercholesterolemia, and diseases associated with atherosclerosis.

In the preferred embodiment, the C-tail protein is administered orally in an amount effective to reduce cholesterol intake from food as measured by a reduction in cholesterol levels in the blood. The dosage will vary depending on the formulation, the rate of excretion, individual variations such as the number of receptors on the intestinal surface, the cholesterol levels to be decreased, and the frequency of administration, as well as other factors routinely optimized by physicians.

The cholesterol uptake from diet by the intestine is about 200 mg/day/person. Cholesterol synthesized by the body is about 500 mg/day/person. The pancreas secrets cholesterol at about 500 mg/day/person, which is reabsorbed through the intestine. Thus, the C-tail competition at the intestinal surface must be effective to reduce the amount of cholesterol from an uptake of about 700 mg cholesterol/day/person. If the reduction is to a level less than 500 mg/day, the body reduce body cholesterol. [PLEASE ADVISE HOW TO REWORD THIS CONCLUSION]

Pharmaceutical compositions containing C-tail protein, designed to improve the pharmaceutical activity of the C-tail protein when administered to a patient in an amount effective to reduce cholesterol uptake in the intestine and thereby decrease blood cholesterol levels, can be prepared in combination with appropriate pharmaceutical stabilization compounds, delivery vehicles, carriers, inert diluents, and/or other additives appropriate for enteral (oral) administration according to methods well known in the art. The formulation usually provides for release within the stomach or the intestine. The C-tail protein can be formulated into a liquid, paste, suspension, gel, powders, tablets, capsules, food additives or other standard forms. Pharmaceutically compatible binding agents and/or adjuvant materials can be included as part of the composition. Examples include a binder such as microcrystalline cellulose, gum tragacanth, or gelatin; an excipient such as starch or lactose; a disintegrating agent such as alginic acid, Primogen™, or corn starch; a lubricant such as magnesium stearate or sterotes; aglidant such as colloidal silicon dioxide; a sweetening agent such as sucrose or saccharin; and/or a flavoring agent such as peppermint, methyl salicylate, or orange flavoring. When the dosage unit form is a capsule, it can contain, in addition to material of the above type, a liquid carrier. Other dosage unit forms may further include coatings of sugar, shellac, or other enteric agents. The C-tail protein can be administered as a component of a fluid such as an elixir, suspension, beverage, liquid dietary supplement or substitute, or syrup; or of a solid such as a wafer or candy. The C-tail protein can also be mixed with other active materials that do not impair the desired action, or with materials that supplement the desired action, such as other blood lipid-lowering pharmaceutical compositions.

In one preferred embodiment, C-tail protein is encapsulated within carriers that effect release in the small intestine, such as microparticles, microcapsules, or microspheres prepared from synthetic or natural polymers such as proteins, polyhydroxy acids, or polysaccharides. Appropriate systems are known to those skilled in the art. Several microsphere formulations have been proposed as a means for oral drug delivery. These formulations generally serve to protect the encapsulated compound and to deliver the compound into the blood stream. Enteric coated formulations have been widely used for many years to protect drugs administered orally, as well as to delay release. Other formulations designed to deliver compounds into the blood stream, as well as to protect the encapsulated drug, are formed of a hydrophobic protein, such as zein, as described in PCT/US90/06430 and PCT/US90/06433; "proteinoids", as described in U.S. Pat. No. 4,976,968 to Steiner; or synthetic polymers, as described in European Patent application 0 333 523 by the UAB Research Foundation and Southern Research Institute. EPA 0 333 523 described microparticles of less than ten microns in diameter that contain antigens, for use in oral administration of vaccines. Larger sizes are preferred for the uses described herein to avoid uptake into the blood and lymph systems of the encapsulated C-tail protein.

The microparticles can be formed of rapidly bioerodible polymers such as poly[lactide-co-glycolide], polyanhydrides, and polyorthoesters, whose carboxylic groups are exposed on the external surface as their smooth surface erodes; natural polymers such as proteins, like zein, modified zein, casein, gelatin, gluten, serum albumin, or collagen, and polysaccharides, like cellulose, dextrans, polyhyaluronic acid, polymers of acrylic and methacrylic esters and alginic acid; synthetic polymers such as polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes and copolymers thereof; and synthetically modified natural polymers such as alkyl celluloses, hydroxyalkyl celluloses, cellulose ethers, cellulose esters, and nitrocelluloses. Representative polymers include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly (ethylene oxide), poly(ethylene terephthalate), poly(vinyl acetate), polyvinyl chloride, polystyrene, polyvinyl pyrrolidone, and polyvinylphenol. Specific representative bioerodible polymers include polylactides, polyglycolides and copolymers thereof, poly(ethylene terephthalate), poly (butyric acid), poly(valeric acid), poly(lactide-co-caprolactone), poly[lactide-co-glycolide], polyanhydrides, polyorthoesters, blends, and copolymers thereof.

These polymers can be obtained from sources such as Sigma Chemical Co., St. Louis, Mo., Polysciences, Warrenton, Pa., Aldrich, Milwaukee, Wis., Fluka, Ronkonkoma, N.Y., and BioRad, Richmond, Calif. or else synthesized from monomers obtained from these suppliers using standard techniques.

Pharmaceutical compositions containing C-tail protein must be stable under the conditions of manufacture and storage and may be preserved against contamination by microorganisms, such as bacteria and fungi, through the use of antioxidants such as Vitamin E and ethoxyquin and bacteriostatic agents, which are on the list of compounds approved for use by the Food and Drug Administration.

As noted above, inactivation and excretion rates of the C-tail protein, as well as other factors known to those of skill in the art, will affect the amount of drug which is administered to a patient. The determinative criteria is whether the amount is effective to reduce the blood cholesterol. Blood cholesterol levels are assayed by standard techniques used by clinical laboratories.

The C-tail protein can be used to reduce the uptake of cholesterol by the intestine and thereby for the treatment of hyperlipidemias including hypercholesterolemia, hypertriglyseridemia and associated disease states such as atherosclerosis, cardiovascular disease, and pancreatitis. The C-tail protein can also be used in normal subjects as a preventative measure to prevent the occurrence of these disorders. It is preferable that human serum cholesterol levels be maintained below 200 mg/dl, with values of 240 mg being considered clinically high and values of 160 mg being considered to be low.

The formulation is administered as a single daily dose or divided daily doses, most preferably three doses given before, during, or after meals. Patients can be maintained on C-tail protein indefinitely to reduce the uptake of cholesterol by the intestine. Conditions to be considered in selecting dosage level, frequency, and duration primarily include the severity of the patient's disorder, the patient's serum cholesterol level, adverse side effects such as gastric distress, and the patient's need for preventive therapy, as well as the therapeutic efficacy. It is to be understood that for any particular subject, specific dosage regimens should be adjusted over time according to the individual patient need and the professional judgment of the person administering or supervising the administration of the compositions, and that the concentration ranges set forth herein are exemplary only and are not intended to limit the scope or practice of the claimed composition. Other concentration ranges and dosage durations can be determined by routine experimentation. An initial estimate of the dosage is based on the calculation that 20 μg is needed to block the receptor binding from 1 cm of the intestine and, therefore, 20 mg of C-tail protein should be enough to cover 10 meters in length of the intestine for blocking the BAL binding sites. A five-fold excess (100 mg) should be more than sufficient for preventing cholesterol absorption by the intestinal cells. Further adjustment of the dosage will be based on the monitoring of the dosage response of patients to C-tail protein in lowering blood cholesterol.

The present invention will be further understood with reference to the following non-limiting examples. All literature citations are expressly incorporated herein by reference.

EXAMPLE 1

Proline-rich Domain and Glycosylation are not Essential for the Enzymatic Activity of Bile Salt-activated Lipase.

To test the functional requirements of the structural regions in the BAL molecule, the truncated human milk bile salt-activated lipase (T-BAL) cDNA (without the mucin-like caroxy terminal region, residues 539–722) was expressed from the T7 system in *Escherichia coli* and purified, and the properties of the truncated recombinant enzyme were studied. The methods were as follows.

Abbreviations.

The following abbreviations are used in this example: PANA, p-nitrophenyl acetate; PANB, p-nitrophenyl butyrate; SDS, sodium dodecyl sulfate; T-BAL, truncated form of bile salt-activated lipase; PCR, polymerase chain reaction; TN (50 mM Tris-HCl, pH 8.0, and 100 mM NaCl); EGTA, ethylene glycol-bis(β-aminoethyl ether)N,N,N',N'-tetraacetic acid; FPLC, fast protein liquid chromatography; and BSA, bovine serum albumin.

Materials.

The purification of BAL from human milk was performed as described in Baba et al. (1991), incorporated herein by reference. The λgt10 cDNA library from human lactating breast tissue was purchased from Clontech (Palo Alto, Calif.). Glycerol tri[9,10-$^{1}$H]oleate was obtained from Amersham (Arlington Heights, Ill.). The oligonucleotides Primer I (Sequence ID No. 4) and Primer II (Sequence ID No. 5), were prepared by Dr. K. Jackson in the Molecular Biology Resource Facility, Oklahoma University Health Science Center. All other chemicals were purchased from Sigma Chemical Co. (St. Louis, Mo.).

Molecular Biology Methods.

Standard methods for sequencing analyses, restriction enzyme treatments, ligation, and subcloning, as described in commonly known and used reference technique publications, Sambrook et al., *Molecular Cloning, A Laboratory Manual*, Cold Spring Harbor Laboratory Press, Cold Spring Harbor, N.Y. (1989); and Ausuble et al. (Eds.), *Current Protocols in Molecular Biology*, Green Publishing Associates and Wiley-Interscience, New York, N.Y. (1989). The cDNA clones G10-2 and G10-5 were isolated from human mammary gland cDNA as described in U.S. Pat. No. 5,200,183 to Tang and Wang. DNA sequencing analyses were performed using a DNA sequencing kit from United States Biochemical Corp. (Cleveland, Ohio) as described below. Double stranded DNA templates were first denatured as described by Kraft et al., *BioTechniques* 6:544–547 (1988). Then 2.5 μg of DNA, 15 ng of primer and 2 μl of reaction buffer were combined in a total volume of 10 μl and heated to 65° C. for 2 min, then cooled to 25° C. over a period 30 min to anneal the template. Labeling mixture was diluted 5-fold with water and Sequenase version 2.0 was diluted 8-fold with water. 1 µl of DTT (0.1M), 2 µl of diluted labeling mix, 5 µCi of [α$^{32}$P]dATP and 2 µl of diluted Sequenase were added to the annealed template-primer. After mixing the tubes were incubated at room temperature for 3 minutes. 2.5 µl of the termination mixture were placed in tubes. The tubes were pre-warmed at 37° C. for 1 minutes. 3.5 µl of labeling reaction mixture was transferred to each termination tube, mixed and then incubated at 37° C. for 3 minutes. The reactions were stopped by adding 4 µl of stop solution. Samples were then run on a 6% acrylamide gel. Prior to the application of samples, the gel was pre-run at a constant voltage of 2000 volts for 30 minutes. Samples were heated at 75° C. for 2 minutes immediately before loading 2 µl onto the sequencing gel. The gels was run at a constant voltage of 2000 for 3 to 4 hours. After the run, the gel was transferred 3MM paper then dried at 80° C. under vacuum for 2 hours. Kodak X-Omat™ PR film was exposed at room temperature overnight for the subsequent reading of the DNA sequence. PCR was performed as described by Innis and Gelfand, in *PCR Protocols. A Guide to Methods and Application* 3–12 (Innis et al. (Eds.), Academic Press, New York, N.Y. (1990)), incorporated herein by reference. The PCR generated DNA was subcloned into PCRII using the TA cloning kit from Invitrogen (San Diego, Calif.) as described below. Ligation with the PCRII vector were set up as 1:1 and 1:3 molar ratio of vector:PCR product. 1 µl of 10× ligation buffer, 50 ng of vector, PCR product and 4 units of T$_4$ DNA ligase were combined in a total volume of 10 µl. The ligation reaction were incubated at 12° C. overnight. 1 µl of each ligation reaction was then added to 50 µl of INVαF' competent cells containing 2 µl of 0.5M β-mercaptoethanol. The tubes were incubated on ice for 30 minutes. The tubes were then placed in a 42° C. water bath for 30 seconds then returned to ice for 2 minutes. 450 µl of room temperature SOC was added to each tube. The tubes were then incubated at 37° C., and shaken at 225 rpm for 1 hour. The transformed cells were spread onto LB plates containing 50 µg/ml kanamycin and 1 mg of X-Gal. The plates were then inverted and incubated at 37° C. overnight for the selection of the transformed clones. Plasmid isolation was performed using the Magic Miniprep™ system supplied by Promega (Madison, Wis.). Three ml of overnight culture was centrifuged at 4000 rpm for 5 minutes to pellet the cells. The pellet was suspended in 200 µl of Cell Resuspension Solution. 200 µl of cell lysis solution was added and mixed by inverting the tubes until the suspension cleared. 200 µl of Neutralization Solution was added and mixed by inverting the tubes several times. A Minicolumn was attached to a syringe barrel and the assembly was inserted into a vacuum manifold. The resin/DNA mixture was transferred to the syringe barrel and poured into the column by applying vacuum. The column was washed with 2 ml of Column Wash Solution and the resin was dried. The minicolumn was centrifuged at 14000 rpm for 20 sec. to remove the remaining wash solution. The DNA was eluted from the column by applying 50 µl of 70° C. water to the column then centrifuge the column after 1 minute for 20 seconds.

Construction of Vector.

The unique SmaI restriction site of the overlapping clones G10-2 and G10-5 was utilized for construction of the cDNA G10-6 to encompass the entire coding sequence region of BAL. PCR was used for preparing T-BAL cDNA with the use of Primers I and II for expression of the truncated form of BAL. The T-BAL cDNA was ligated to the pET11a cloning vector (Invitrogen, San Diego, Calif.) at the NdeI/BamHI cloning site for the subsequent expression of T-BAL using the T7-expression system in *E. coli*.

Expression of T-BAL Using pMT11a Vector.

The general approach and methodology for using T7 polymerase to direct the expression of the cloned genes are described by Studier et al., *Methods Enzymol.* 185:60–89 (1990), incorporated herein by reference. The cDNA of T-BAL was ligated to the NdeI/BamHI cloning sites of pET11a (Novagen, Madison, Wis.). The vector was used to transform the *E. coli* BL21 (DE3) for the expression of T-BAL. The cells harboring the vector were cultured overnight in ZB medium (Studier et al. (1990)) with ampicillin. The next morning 4 liters of LB-ampicillin were incubated with 80 ml of the overnight culture, which was shaken at 37° C. until absorbance at 600 nm reached 0.6. Isopropyl-β-D-thiogalactopyranoside was then added to a concentration of 0.4 mM with shaking for 3 hours. The cells were collected by centrifugation and resuspended in 800 ml TN buffer (50 mM Tris-HCl, pH 8.0, and 100 mM NaCl) with 80 mg lysozyme. The mixture was frozen at −70° C. and then thawed in a 37° C. water bath, for three cycles. The solution was diluted to 2,400 ml with TN and centrifuged at 16,000×g for 15 minutes. The pellet (inclusion bodies) was then washed twice with Triton™ X-100 (0.1%) in TN, and the pellets recovered by centrifugation and kept frozen at −20° C. for further processing.

Refolding and Purification of T-BAL.

The frozen inclusion bodies were further solubilized by stirring with 60 ml of 8M urea in 100 mM Tris-HCl, pH 12.5, containing 1 mM EGTA (ethylene glycol-b(β-aminoethyl ether)N,N,N',N'-tetraacetic acid), 10 mM β-mercaptoethanol and 5% glycerol (v/v). This mixture was centrifuged at 105,000×g for 30 minutes, and the supernatant was then placed in a dialysis tubing (exclusion MW=10, 000) and dialyzed against 1 liter of a refolding buffer containing 1M urea, 0.1 mM β-mercaptoethanol, and 5% glycerol in 10 mM Tris-HCl, pH 8.0. After dialysis for 20 hours, the refolded T-BAL was assayed for esterase activity, as described under "Esterase Assay" below, using 1 mM PANA as substrate and 2 mM taurocholate as activator to determine the amount of active enzyme in the dialyzed solution. The refolded T-BAL was then mixed with 60 ml of saturated ammonium sulfate (adjusted to pH 8.0 with NH$_4$OH), which caused the precipitation of T-BAL. The T-BAL was collected from the precipitate after centrifugation at 18,000 rpm for 1 hour. The collected precipitate was solubilized with 40 ml of the refolding buffer and stirred at 4° C. for 30 minutes. The supernatant fraction was then concentrated to 3 to 5 ml in an Amicon Centriprep™-10 concentrator (Beverly, Mass.). After further ultracentrifugation at 105,000×g for 30 minutes, the supernatant fraction (1 ml) was subjected to molecular sieving fractionation by fast protein liquid chromatography (FPLC). Two Superose™ 12 columns (Pharmacia, Piscataway, N.J.) were linked in tandem for the FPLC fractionation. The columns were equilibrated and eluted with a buffer solution containing 1M urea, 0.15M NaCl, 0.1 mM β-mercaptoethanol, and 50 mM Tris-HCl, pH 8.0. The column was eluted with a flow rate of 0.5 ml/minutes. The eluate was collected in 1 ml fractions and monitored by measuring absorbance at 280 nm and by assaying esterase activity with PANA as substrate.

N-terminal Amino Acid Sequence Analysis.

Automated Edman degradations were performed according to Hewick et al., *J. Biol. Chem.* 256:7990–7997 (1981), incorporated herein by reference, in a Model 470A gas-phase protein sequencer equipped with a Model 120A on-line phenylthiohydantoin amino acid analyzer (Applied Biosystems, Inc., Foster City, Calif.).

Esterase Assay.

The kinetic studies of BAL esterase activity with short chain esters were performed using p-nitrophenyl acetate (PANA) and p-nitrophenyl butyrate (PANB) as substrates, as described in Wang, *Biochem. J.* 279:297–302 (1991), incorporated herein by reference. For deducing the Michaelis-Menten kinetic parameters, the experiments were performed at 25° C., and the range of the substrate concentration in the final assay mixtures was 0.4 to 2 mM for PANA and 0.1 to 0.5 mM for PANB, with 2 mM taurocholate as activator. The rate of p-nitrophenol production was determined from the initial portion of the absorbance change (20 seconds) at 418 nm using a Hewlett-Packard Diode Array Spectrophotometer (Hewlett Packard, Palo Alto, Calif.) equipped with a peltier temperature control. For monitoring the refolding efficiency, as well as the esterase activity in column chromatography eluants and the specific activity of the purified enzyme, the enzyme assays were performed with 1 mM PANA as substrate and 2 mM taurocholate as activator. One unit of enzyme activity was defined as one μmole of the product released per minute.

Thermostability of T-BAL.

For determining the thermostability, 0.1 mg/ml each of T-BAL and native BAL in sodium phosphate (0.15M, pH 7.4) were incubated for 10 minutes in a water bath at 30° C., 40° C., 45° C. and 50° C. for 10 minutes. After incubation, the solutions were cooled in ice-water. These treated samples were then assayed for remaining activity with PANA as substrate.

Lipase Assay.

The lipase assay of BAL was performed according to a modification of the method of Nilsson-Ehle and Schotz, *J. Lipid Res.* 17:536–541 (1976), incorporated herein by reference, using glycerol tri[9,10-$^3$H]oleate as substrate. The two-fold concentrated stock substrate solution was prepared by emulsifying 28 μmol of trioleoylglycerol (specific activity 1.4 μCi/μmol) and 2.8 μmol of dioleoylphosphatidylcholine in 10 ml of 50 mM NH$_4$OH-HCl buffer, pH 8.5. The mixture was emulsified using a W-380 sonicator (Heat Systems-Ultrasonics, Inc., Farmingdale, N.Y.) at a setting of 5 (50% maximum output) for 30 seconds in an ice bath. After cooling, the mixture was further sonicated for an additional 30 seconds. The assay mixture with final volume of 100 μl contained 50 mM NH$_4$OH-HCl buffer, pH 8.5, 1.4 mM trioleoylglycerol, 0.14 mM dioleoylphosphatidylglycerol, taurocholate, and 10 μl of the enzyme solution. Following a one-hour incubation at 37° C. with agitation, the reaction was terminated by the addition of 3.2 ml of chloroform-heptane-methanol (5:4:5.6, vol/vol/vol) and 1 ml of 0.2M NaOH. Samples were centrifuged and mixed with 10 ml of Hydrocount™ (J. T. Baker, Inc., Phillipsburg, N.J.), and the radioactivity was determined in a Beckman scintillation counter (Fullerton, Calif.).

Sodium Dodecyl Sulfate (SDS)-Polyacrylamide Gel Electrophoresis.

The SDS-polyacrylamide gel electrophoresis was performed using the LKB-Pharmacia Phast system (Piscataway, N.J.) and with a 8–25% polyacrylamide gel slab manufactured by Pharmacia (Piscataway, N.J.). The samples were treated with 10 mM β-mercaptoethanol and 2% SDS at 100° C. for 6 minutes prior to electrophoresis.

Protein Assay.

The protein content of the enzyme preparation was determined by a modification (Wang and Smith, *Anal. Biochem.* 63:414–417 (1975), incorporated herein by reference, of Lowry's procedure using serum albumin as standard (Lowry et al., *J. Biol. Chem.* 193:265 (1951).

Fluorescence Measurement of the Interaction of T-BAL with Taurocholate.

Fluorescence measurements of the interaction of T-BAL with taurocholate were made at 25° C. with the aminco-Bowman Series 2 Fluorescence Spectrometer (Urbana, Ill.). The T-BAL tryptophanyl fluorescence was used for studying the interaction of T-BAL with taurocholate. Fluorescence was recorded at 340 nm with excitation wave length at 280 nm. The band-width of excitation and emission were both set a 2 nm. The sensitivity of the instrument was set at 1,000 volts of the detector high voltage.

When taurocholate (the activator) was not present, the fluorescence intensity of T-BAL was $F°$. At the saturating concentration of taurocholate, the fluorescence intensity was $F_\infty$. Based on the fluorescence (F) at a specified taurocholate concentration, the molar fraction (x) of T-BAL that is associated with taurocholate was determined by relating the F, as shown in the following equation:

$$F = (1-x)F_o + xF_\infty$$

The deduced molar fraction (x) is then used for calculation of the taurocholate and T-BAL binary complex dissociation constant $K_A$. Conversely, the computer least-square curve-fitting procedure to treat $K_A$ and $F_\infty$ as the variable parameters can be used for achieving the best agreement with the calculated and the experimentally determined values of F.

Data Analysis.

Kinetic analysis of data generated in these experiments was performed using a LOTUS 1-2-3 SPREAD SHEET program (Worcester, Mass.) and an IBM-AT computer. The performance of least-square non-linear curve fitting was done according to the approach described by Bevington, in *Data Reduction and Error Analysis for the Physical Sciences* 56–65 and 204–246, McGraw-Hill, New York (1969), incorporated herein by reference.

(a) The carboxyl-terminal domain, O-glycosylation, and N-glycosylation are not essential for the enzymatic function of BAL.

The amino acid sequence of native human milk BAL cDNA (Baba et al. (1991); Hui and Kissel, *FEBS Lett.* 276:131–134 (1990); Nilsson et al., *Eur. J. Biochem.* 192:543–550 (1990)) encodes for a 722-residue mature enzyme and is shown in Sequence ID No. 3. The cDNA structure is identical to that of the pancreatic BAL (Reue et al., *J. Lipid Res.* 32:267–276 (1991)), supporting the concept that the enzyme from mammary gland and from pancreas are expressed from the same gene.

As expected, the T-BAL synthesized in *E. coli* is inactive and is insoluble in aqueous buffer. Active T-BAL was obtained by refolding. This procedure included the solubilization of the inclusion bodies with urea and β-mercaptoethanol at a high pH (12.5), followed by dialysis against a low concentration of urea at lower pH (8.0). Based on the enzyme activity measurement, the yield of the active enzyme was about 10 mg per 4 liters of the cultured LB-medium. SDS-polyacrylamide gel electrophoresis gave rise to a major protein (greater than 90%) in the urea-soluble fraction corresponding to a molecular weight of 60,000, which approximated closely the expected molecular weight of T-BAL (59,270). N-terminal sequence analysis of this protein fraction gave the expected BAL N-terminal sequence of Ala-Lys-Leu-Gly-Ala-Val-Tyr-Thr-, (amino acids 1 to 8 of Sequence ID No. 1), indicating the successful synthesis of T-BAL and the removal of initiation methionine. The specific activity of T-BAL after the initial step of the refolding was about 5 to 10 units/mg, which is only 10 to 20% of that of the native BAL.

The recombinant T-BAL expressed in *E. coli* is not glycosylated, indicating further that the highly glycosylated C-terminal region of BAL is not essential for catalytic function.

Purification of T-BAL was achieved by molecular sieving with FPLC after prior partial purification of the refolded T-BAL with ammonium sulfate precipitation. Two major peaks were found in the column fractions. The first peak, eluted at the void volume (17 ml), represents the major protein peak and contains mainly the aggregate form of the inactive T-BAL. The second peak (eluted at 28 ml) contains BAL activity. SDS-polyacrylamide gel patterns of fractions 27-29 indicate that T-BAL eluted in this peak was homogeneous. From four individual batches, an average specific activity of 64±2 units/mg for the purified enzyme (fraction 28) was obtained. The FPLC column chromatography effectively separated the active from the inactive forms of the enzyme, since this specific activity of T-BAL is higher than that reported for the native BAL (52 units/mg) reported previously (Wang and Johnson (1983)).

(b) Kinetic and specificity

With the availability of a sufficient amount of purified recombinant T-BAL, the specificity and kinetics of T-BAL and the native BAL were compared and other characteristics were noted.

Thermostability of T-BAL.

To compare the stability of T-BAL with the native enzyme, these two enzyme forms were treated at temperatures ranging for 30° C. to 50° C. The heat inactivation patterns for T-BAL and native BAL were similar, with both showing a loss of about 90% of activity with treatment at 50° C. for 10 minutes. This further suggests that the folding of T-BAL is similar to that of the catalytic domain of the native enzyme.

Taurocholate Binding Kinetics of T-BAL.

The dissociation constants $K_A$ of T-BAL and native BAL are similar. In a direct binding study of the tryptophanyl fluorescence upon interaction with taurocholate, native BAL upon binding with the bile salt showed about 20% decrease of the protein tryptophanyl fluorescence at a saturating concentration of taurocholate (Wang and Kloer (1983)), which probably resulted from a conformational change of BAL upon ligand binding. The dissociation constant of native BAL is 0.37 mM. (Wang, *J. Biol. Chem.* 256:10198–10202 (1981)). A similar decrease of tryptophanyl fluorescence was observed with T-BAL, in which α and β are the two parameters utilized for expressing the activation effect of taurocholate by modifying the kinetic parameters $K_s$ and $k_{cat}$, respectively (Segel, *Enzyme Kinetics* 227-231, John Wiley & Sons, New York (1975)). Based on a 1:1 stoichiometry, the dissociation constant $K_A$ of 0.32±0.03 mM (n=4) was determined for the T-BAL and taurocholate interaction. There was an 18% decrease of fluorescence intensity at a saturating concentration of taurocholate. Thus, T-BAL has a slightly higher affinity to the monomeric form of taurocholate compared with the native enzyme. These results indicate that the microenvironment of taurocholate binding sites of T-BAL and native BAL are very similar despite the deletion of the proline-rich sequence domain of T-BAL.

Kinetic Properties of T-BAL with PANA and PANB.

Further kinetic analysis indicated that there are enzyme specificity changes revealed with the use of PANA and PANB (p-ntirophenyl butyrate) as substrates.

Similar to the native BAL, T-BAL was found to contain basal activity when assayed in the absence of bile salts with the esterase substrates. Therefore, taurocholate can also be considered as a non-essential activator of T-BAL. From the Lineweaver-Burke plots, the kinetic parameters $K_s$, $k_{cat}$ (for basal enzyme) and $\alpha K_s$, and $\beta k_{cat}$ (taurocholate-activated enzyme) for T-BAL and PANA and PANB as substrates were obtained. Despite the fact that a slightly higher specific activity of T-BAL (64 units/mg) than that of native enzyme (52 units/mg) (Wang and Johnson (1983)) was obtained, the derived $k_{cat}$ and $\beta k_{cat}$ of T-BAL was about 2 to 8 fold lower than that of the native enzyme. However, the deduced $K_s$ and $\alpha K_s$ of T-BAL were only slightly higher than that of the native enzyme. Thus, the presence of the proline-rich sequence plays a role mainly in enhancing the turnover rate of the enzyme, but has only a minor effect on the substrate binding affinity. In addition, there is a change of the preferential reactivity of the enzyme. Previously it was reported that among the short chain acyl-esters of p-nitrophenol, native BAL has the highest $k_{cat}$ and $\beta k_{cat}$ with PANB. In contrast, T-BAL has a higher $k_{cat}$ and $\beta k_{cat}$ with PANA than with PANB, when assayed in the presence of taurocholate. Despite this, T-BAL also has higher substrate specificity constants ($k_{cat}/K_s$ and $\beta k_{cat}/\alpha K_s$ of T-BAL with PANB. This is similar to what is found for the native enzyme. The activation effect of taurocholate on BAL-catalyzed hydrolytic reaction with PANA as substrate demonstrates that the proline-rich domain of BAL does not represent the bile salt-binding site of the enzyme.

Lipase Activity of T-BAL.

There is an essential requirement of bile salt micelles acting as fatty acid acceptors in the native BAL-catalyzed hydrolysis of long chain triacylglycerol (Wang et al. (1988)). The hydrolysis of glycerol was compared in native BAL and T-BAL. In this respect, T-BAL was found to have a requirement similar to that of native BAL for a bile salt in the hydrolysis of long-chain trioleoylglycerol. Since serum albumin is not a fatty acid acceptor for BAL catalysis, it is also a poor fatty acid acceptor in the BAL-catalyzed reaction; thus only taurocholate, and not BSA, was included in the lipase mixture as the fatty acid acceptor.

There is an apparent saturation of activation of the native BAL catalysis when taurocholate concentration is above 60 mM, attributable to the partial inactivation of the native BAL when taurocholate concentration is high. In contrast, there was apparent non-saturable activation of T-BAL by micellar taurocholate (up to 120 mM taurocholate tested). The apparent saturation of the activation by taurocholate above 60 mM, on the other hand, is likely due to the partial inactivation of the enzyme when the taurocholate concentration is high. These results indicate that the transfer of fatty acid product from the enzyme active site is probably not through a receptor mediated process but through second order reaction kinetics involving the enzyme-fatty acid complex and the taurocholate micelles.

EXAMPLE 2 the Function of the C-Tail of BAL is to Bind BAL to the Intestinal Epithelial Lining Cells.

(a) Binding of human milk BAL to intestinal mucosa.

Experiments were conducted to determine that human milk BAL binds to the intestinal mucosa by (i) radiolabeling ($I^{125}$) purified native human milk BAL, (ii) incubating radio-labeled BAL inside isolated mouse intestine, (iii) determining the extent of intestinal retention of labeled BAL, and (iv) examining the mechanism of binding the BAL to intestine by examining the elution of the mouse endogenous BAL with galactose, fucose, heparin, 0.3M NaCl and with using isotonic phosphate buffer as control.

Methods.

Purification of human milk BAL was performed as described by Wang and Johnson, *Anal. Biochem.* 133:457–461 (1983), incorporated herein by reference. Preparation of a truncated form of recombinant BAL (T-BAL) was performed as described in Example 1.

The iodination of human milk BAL and recombinant T-BAL was performed using iodo beads (Pierce, Rockford, Ill.). Iodine$^{125}$ was obtained from Amersham (Arlington Heights, Ill.). The iodination was performed by adding 6 μl of $^{125}$I to 94 μl of the enzyme solution (2 mg/ml in sodium phosphate buffer, pH 6.5). One washed bead was placed in the solution and let stand at room temperature for 15 minutes. The mixture was then passed through a Bio-spin™ 6 column (Bio Rad, (Hercules, Calif.) and centrifuged at 2275 rpm for 4 minutes at 4° C. and the eluate collected. The eluate was diluted with 400 μl of 0.1M sodium phosphate buffer, pH 6.5. The eluted fractions were combined and 1 μl of the eluate was examined for radioactivity. The lipase assay of BAL was performed a described in Example 1 using glycerol tri[9,10-$^3$H]oleate as substrate. The two-fold concentrated stock substrate solution was prepared by emulsifying 28 μmol of trioleoylglycerol (specific activity 1.4 μCi/μmol) and 2.8 μmol of dioleoylphosphatidylcholine in 10 ml of 50 mM NH$_4$OH-HCl buffer, pH 8.5. The mixture was emulsified using a W-380 sonicator (Heat Systems-Ultrasonics, Inc., Farmingdale, N.Y.) at a setting of 5 (50% maximum output) for 30 seconds in an ice bath. After cooling, the mixture was further sonicated for an additional 30 seconds. The assay mixture with final volume of 100 μl contained 50 mM NH$_4$OH-HCl buffer, pH 8.5, 1.4 mM trioleoylglycerol, 0.14 mM dioleoylphosphatidylglycerol, 30 mM taurocholate, and 10 μl of the enzyme solution. Following a one hour incubation at 37° C. with agitation, the reaction was terminated by the addition of 3.2 ml of chloroform-heptane-methanol (5:4:5.6, vol/vol/vol) and 1 ml of 0.2M NaOH. Samples were centrifuged and mixed with 10 ml of Hydrocount™ (J. T. Baker, Inc., Phillipsburg, N.J.), and the radioactivity was determined in a Beckman scintillation counter (Fullerton, Calif.).

Protocol for binding of $^{125}$I-labeled BAL and T-BAL to mouse small intestine.

The duodenum and jejunum were removed from mouse (about 20 grams each) small intestine and cut into 12-cm segments. Three experiments were performed in which T-BAL, without the C-tail, was used in parallel experiments as a control. The segments were washed once with 0.15M NaCl and twice with 0.1M sodium phosphate buffer, pH 6.5. Twenty μl of the labeled samples were first mixed with 20 μl of 8M urea and then diluted with 720 μl distilled water and 240 μl 20% albumin with a final volume of 1 ml. Five hundred μl of the solution were then injected into each intestinal segment with both ends ligated. The segments were incubated at room temperature for two hours. After incubation, the intestine was washed three times with 0.1M sodium phosphate buffer, pH 6.5, and 2 cm of the intestinal pieces were cut for counting the radioactivity.

Figure 2:
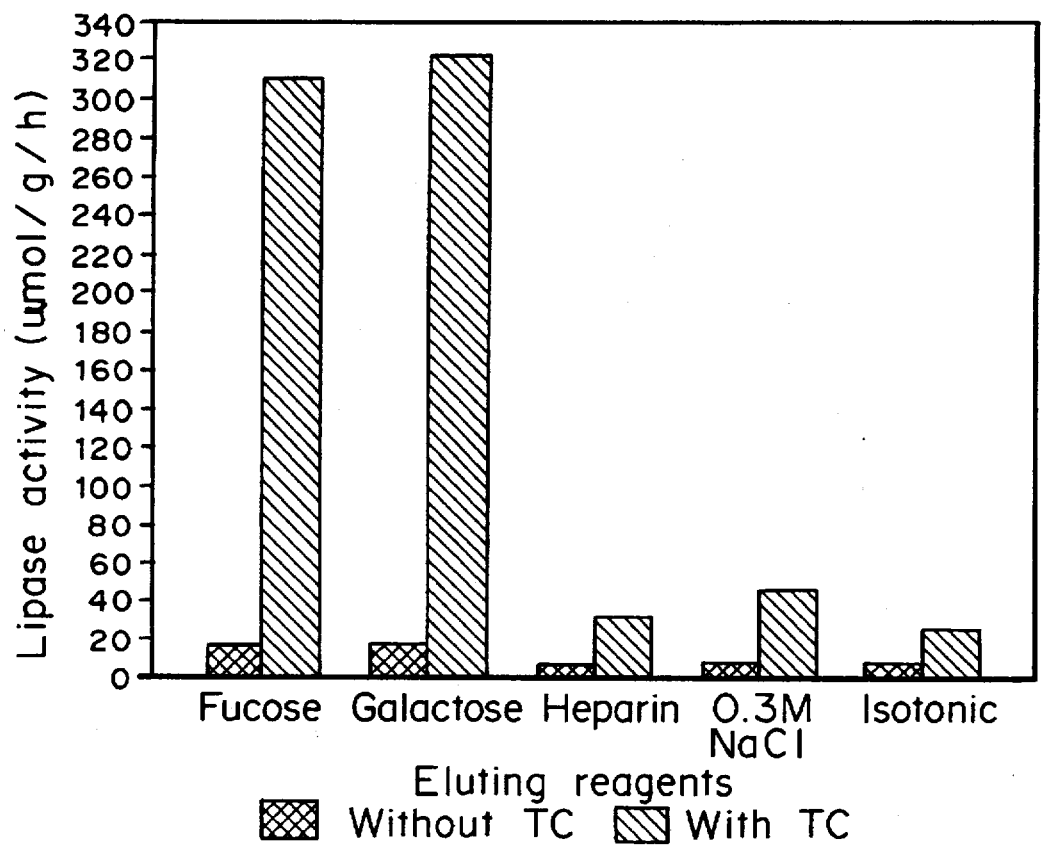
FIG. 2 shows the elution of endogenous BAL lipolytic activity, measured in μmol/g/h from mouse intestinal mucosa using either isotonic phosphate buffer, fucose (0.1M), galactose (0.1M), heparin (10 mg/ml), or NaCl (0.3M).

The results of these experiments are shown in Table II, Table III, and Table IV, and in FIG. 2.

TABLE II

Binding of I$^{125}$-labeled BAL and T-BAL to mouse small intestine.

| | Bound ng/cm | |
|---|---|---|
| | BAL | T-BAL |
| Exp. 1 | 272 | 42 |
| Exp. 2 | 353 | 31 |
| Exp. 3 | 527 | 25 |
| Mean | 384 | 33 |
| ±SD | 130 | 9 |

Average from 3 experiments.

TABLE III

Individual experiments examining binding of I$^{125}$-labeled BAL and T-BAL to mouse small intestine.

| Experiment 1 | | Experiment 2 | | Experiment 3 | |
|---|---|---|---|---|---|
| BAL (ng/cm) | T-BAL (ng/cm) | BAL (ng/cm) | T-BAL (ng/cm) | BAL (ng/cm) | T-BAL (ng/cm) |
| 286 | 57 | 424 | 47 | 568 | 0.41 |
| 346 | 41 | 488 | 32 | 494 | 13.62 |
| 284 | 32 | 275 | 32 | 312 | 44.73 |
| 172 | 39 | 224 | 12 | 734 | 41.27 |
| Mean | | | | | |
| 272 ± 73 | 42 ± 11 | 353 ± 124 | 31 ± 14 | 527 ± 175 | 25 ± 22 |

In these experiments, native BAL was retained by the intestinal mucosa in amounts nearly twelve times greater than T-BAL, as shown in Table II and Table III. Since the native BAL and T-BAL differ only in C-tail, these results indicate that the attachment to intestinal surface is mediated by the glycosylated C-tail, possibly to a receptor on the intestinal surface.

To determine whether pancreatic BAL attaches to the surface of the intestine in an adult animal, BAL enzymatic activity was measured in mouse intestine after the segments were thoroughly washed with physiological saline. The results demonstrated that the intestine possessed high BAL activity.

To examine the nature of interaction between BAL and the mouse small intestine receptor, experiments were conducted to elute the endogenously bound BAL enzymatic activity from the intestinal mucosa by incubating a 1 cm segment of the washed intestine with fucose, galactose, heparin, NaCl and isotonic phosphate buffer. The results are shown in Table IV.

TABLE IV

Elution of mouse endogenus pancreatic BAL from mouse small intestine.

Elution Buffer:

| Fucose (0.2M) | Galactose (0.2M) | Heparin (10 mg/ml) | 0.3M NaCl | Isotonic phosphate buffer |
|---|---|---|---|---|
| Lipase activity (μmol/g/hr) | | | | |
| Trial 1: | | | | |
| 20[a] 393[b] | 20[a] | 411[b] | 7.7[a] 32.2[b] | 8.8[a] 46.7[b] |

TABLE IV-continued

Elution of mouse endogenus pancreatic BAL from mouse small intestine.

Elution Buffer:

| | Fucose (0.2M) | Galactose (0.2M) | Heparin (10 mg/ml) | 0.3M NaCl | Isotonic phosphate buffer |
|---|---|---|---|---|---|
| Trial 2: | 20[a] | 300[b] | | | 7.9[a] |
| | 13[a] | | | | 25.8[b] |
| | 357[b] | 16[a] | 154[b] | | |
| Trial 3: | | | | | |
| | 16[a] | | | | |
| | 276[b] | | | | |
| Average: | 309 | 19 | 322 | 7.7 | 8.8 |
| | | | | | 7.9 |
| | 16 | | | | |
| Standard deviation: | 74 | 2 | 81 | 32.2 | 46.7 |
| | | | | | 25.8 |
| | 4 | | | | |

[a] without taurocholate (a bile salt): assay for non-specific lipase activity.
[b] with taurocholate: assay for specific BAL activity.

Only low activity of BAL was eluted with isotonic phosphate buffer and with 0.3M NaCl, indicating that BAL is not bound to intestine through ionic interactions. Further, heparin did not elute more BAL activity than those eluted by the isotonic phosphate buffer and by NaCl, indicating that the intestinal binding activity of BAL, which is known to bind heparin, mediated by heparin is not significant. When elution was carried out with either galactose or fucose, however, a large amount of BAL activity was eluted. These results indicate that the binding of BAL to the intestinal lumenal surface is through the oligosaccharide groups in the C-tail. Further, since the elution is very specific, the results indicate the presence of a receptor (CT receptor) that specifically binds the oligosaccharides in the C-tail of BAL.

Mouse pancreatic BAL has a C-terminal region containing four repeating motifs similar to that of the human enzyme. The results above confirm a similarity in the structure of the oligosaccharides, since human BAL binds to mouse intestine.

EXAMPLE 3

BAL elution from intestine.

(a) The elution of rat endogeneous intestinal BAL with galactose, fucose, methyl-α-mannoside, EGTA, heparin and with isotonic phosphate buffer as control.

Because the intestine from mouse is too small in size, rat intestine was used to demonstrate the elution of BAL by various compounds. The initial experiment was to demonstrate that, like the observation done with mouse intestine, the rat endogeneous BAL can also be similarly eluted with galactose and fucose. Since calcium ion is required for the ligand binding of C-type lectin, EGTA elution was included for a test of calcium requirement for the BAL binding to intestinal surface.

Table V shows the results of three experiments which indicate that bound rat intestinal BAL was eluted by galactose (0.1M), fucose (0.1M) and EGTA (1 mM). The elution by heparin (10 mg/ml) was ineffective as the activity in the eluent was low, similar to the level of elution by isotonic phosphate buffer (pH 7.4). In these experiments, 1 cm-segments of the washed rat intestine were incubated for 30 min at room temperature with the eluting compounds dissolved in isotonic phosphate buffer, pH 7.4. The BAL activity in the eluent was assayed as indicated in Example 1.

TABLE V

Elution of rat intestinal BAL with various reagents.

| | galactose (0.1M) | fucose (0.1M) | EGTA (1 mM) | heparin (10 mg/ml) | isotonic buffer |
|---|---|---|---|---|---|
| | BAL activity (μmol/g intestine/h) | | | | |
| EXP1 | 13.01 | 24.25 | 14.54 | 2.09 | 0.99 |
| EXP2 | 16.44 | 26.92 | 21.67 | 1.82 | 0.52 |
| EXP3 | 22.91 | 13.61 | 19.59 | 1.98 | 1.82 |
| AVERAGE = | 17.45 | 21.59 | 18.60 | 1.96 | 1.11 |
| SD = | 3.02 | 7.04 | 3.66 | 0.14 | 0.66 |

The failure of heparin to elute the intestinal bound BAL indicated that BAL is not bound to rat intestine through heparin. These results are in total agreement with the results obtained on the elution of BAL from mouse intestine (Table IV). The successful elution of bound BAL by either galactose or fucose indicates that the binding of BAL to the intestinal lumenal surface is through the oligosaccharide groups in the C-tail. The finding of EGTA eluted BAL indicated the binding of BAL-tail to intestine has a calcium cofactor requirement.

(b) The release of BAL from intestinal epithelial cells was associated with a diminished cholesterol uptake from cholesterol oleate.

Experimental.

Experiments were conducted to demonstrate that the attachment of BAL to the intestinal lining cells is required for the uptake of cholesterol as follows.

A cholesterol (oleate)ester emulsion solution was prepared as follows. A two-fold concentrated cholesterol oleate stock solution was prepared by emulsifying 6 μmol of [$^3$H] cholesterol oleate (1.6 μCi/μmol) (Amersham, Arlington Heights, Ill.) with 0.6 μmol of dioleoylphosphatidylcholine in 15 ml of isotonic phosphate buffer, pH 7.4. The mixture was emulsified using a w380 sonicator (Heat System-Ultrasonics, Inc. (Farmingdale, N.Y.) at a setting of 5 (50% maximum output) for 30 seconds in an ice bath. After cooling, the mixture was further sonicated for an additional 30 seconds.

In each of four experiments, two 12-cm segments of a rat small intestine were excised and washed once with isotonic phosphate buffer, pH 7.4. Segments from each animal were randomly assigned to control (not washed by EGTA) and experimental (washed by EGTA) groups. The use of paired segments from the same animal in the control and experimental groups reduced any differences among animals in the amounts of bound BAL in the intestine. The intestinal segments were ligated at each end and fastened to a catheter at one end, for injection or removal of solutions from the lumen.

Control segments were first injected with 1 ml of isotonic phosphate buffer, pH 7.5. To release the BAL bound to the intestinal surfaces, experimental segments received the same isotonic buffer containing 1 mM EGTA. The intestinal segments were placed on a polystyrene weighing dish (14 cm$^2$) containing 5 ml of the same isotonic buffer and gently shaken for 30 minutes. The experimental segments were then washed once with isotonic phosphate-EGTA solution and twice with the isotonic buffer. The control intestine was washed three times with the isotonic buffer.

To allow uptake of cholesterol by the intestinal segments, a 1 ml aliquot containing 0.2 mM [$^3$H]-cholesterol oleate (Amersham, Arlington Heights, Ill.) and 6 mM taurocholate (Sigma Chemical Co., St. Louis, Mo.), a cofactor for BAL, was then placed in each intestine. After incubation for 60 minutes with gentle shaking in a polystyrene weighing dish, the contents in the intestinal segments were removed. The segments were washed three times with isotonic buffer.

To measure the uptake of radioactive cholesterol by the control and experimental intestinal segments, the central 10 cm of each intestinal segment was removed and further cut into four segments of about 2.5 cm, each of which was placed into scintillation vials containing 1 ml of 2% sodium dodecylsulfate plus 8M urea for the solubilization of the tissue. After the solubilization process, 10 ml of Hydrocount™ (J. T. Baker, Inc., Phillipsburg, N.J.) was added to each vial, and the amount of radioactivity from $^3$H-cholesterol in the intestinal segments was counted using a Beckman Scintillation Counter (Fullerton, Calif.).

Figure 3:
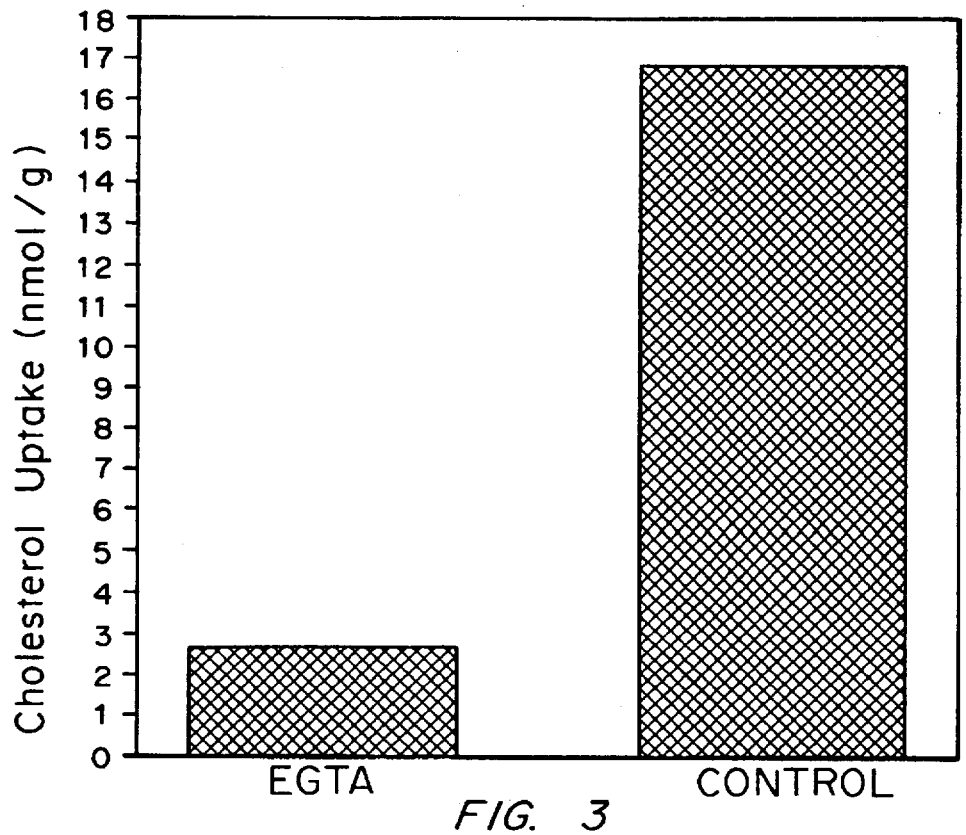
FIG. 3 shows the cholesterol uptake in nmol/g/h of radioactive cholesterol (oleate) ester in rat intestine either treated or untreated with Ethylene-bis(oxyethylenenitrilo)] tetraacetic acid (EGTA) to remove BAL.

The results from the four experiments are shown in Table VI and FIG. 3.

TABLE VI

Effect of Treatment with EGTA on the Cholesterol Uptake of Rat Intestine

| Experiment | EGTA Treatment nmol/g | Control nmol/g | % of control |
|---|---|---|---|
| 1 | 1.41 | 11.65 | 12.10 |
| 2 | 4.25 | 20.40 | 20.83 |
| 3 | 2.85 | 12.78 | 22.30 |
| 4 | 2.23 | 22.28 | 10.01 |
| Average SD | 2.69 | 16.78 | 16.31 |
|  | 1.20 | 5.34 | 6.16 |
|  | P < .005 |  | P < .0001 |

(EGTA = [Ethylene-bis(oxyethylenenitrilo)]tetraacetic acid.)

As shown in Table VI, EGTA treatment reduced cholesterol uptake by intestinal epithelial cells to about 16% of the control uptake. The statistical significance of the raw data (p<0.005) and the data calculated as percent of control (p<0.0001) showed an extremely high confidence level of the difference. These results indicated that BAL, attached to intestinal surface, mediates the uptake of cholesterol from the intestinal lumen by the intestinal lining epithelial cells.

(c) In addition to the role of BAL in the uptake of cholesterol from cholesterol ester, it also mediates the direct uptake of free cholesterol.

Since about 85% of dietary cholesterol is in free cholesterol form, it is important to establish the role of BAL in the uptake of free cholesterol.

An in vitro experiment was carried out to compare the uptake of radioactive cholesterol in control intestines as compared to the intestines from which the bound BAL has been removed by EGTA. Table VII shows the results from three experiments. The mean value of the control experiment was the uptake of 16.38 nmol/g intestine/h. The mean value for the EGTA treated intestine is 4.40 nmol/g intestine/h. The removal of BAL caused a reduction by about 70% of the free cholesterol uptake. In spite of the relatively large variations among three rats, the difference of the two groups is highly significant (p<0.005).

TABLE VII

Free cholesterol uptake by rat intestine (nmol/g/h)

|  | EGTA treated | CONTROL | % OF CONTROL |
|---|---|---|---|
| EXP1 | 5.21 | 17.83 | 29.22 |
| EXP2 | 4.98 | 26.13 | 19.06 |
| EXP3 | 6.00 | 9.95 | 60.30 |
| EXP4 | 2.64 | 14.69 | 17.97 |
| EXP5 | 3.37 | 13.31 | 25.32 |
| MEAN | 4.44 | 16.38 | 30.37 |
| N | 5 | 5 | 5 |
| SE | 0.62 | 2.75 | 7.76 |

A two-fold concentrated cholesterol stock solution was prepared by emulsifying 6 μmol (specific activity=1.6 μCi/μmol) of cholesterol and 0.6 μmol of dioleoylphosphatidylcholine in 15 ml of isotonic phosphate buffer, pH 7.4. The mixture was emulsified using a W-380 sonicator (Heat-System-Ultrasonics,Inc) at a setting of 5 (50% maximum output. for 30 s. in an ice bath. After cooling, the mixture was further sonicated for an additional 30 sec.

Two segments of rat intestine (11 cm) each were washed once with isotonic phosphate buffer (pH 7.4) and the segments were ligated at both ends. One ml of the isotonic phosphate buffer with and without 1 mM EGTA was then injected into each intestine segment. The segment was placed on a polystyrene weighing dish (14 cm square) containing 5 ml of isotonic phosphate buffer. After incubation, the solution in the intestine was replaced with 1 ml of [$^3$H] cholesterol (0.2 mM) and 6 mM taurocholate and the segments were placed on the incubation tray on top of the ice bath as described above. The intestine segments were then washed 3 times with isotonic phosphate buffer and an 8 cm section of each intestine segment (about 0.7 g) was cut into 2 cm pieces and each piece placed in 1 ml of 2% SDS-8M urea for solubilization of the tissue. To this mixture, 10 ml of Hydrocount™ was added for counting radioactivity as described in Example 3a.

(d) Heparin inhibits the uptake of free cholesterol by rat intestine.

The uptake of [$^3$H] cholesterol oleate by rat intestine was studied in vitro in the presence of added heparin (10 mg/ml). The procedure was essentially the same as that described in Example 3b. Table VIII shows that the control (column-1 presence of taurocholate and absence of heparin), the mean uptake is 20.65 nmol/g/h. In the presence of heparin (column 2) is 2.62 nmol/g/h. The difference is significant (p<0.05). The value from heparin inhibition is near that of the background uptake in the absence of taurocholate.

TABLE VIII

EFFECT OF HEPARIN ON THE UPTAKE OF [$^3$H] CHOLESTEROL OLEATE BY RAT INTESTINE DATA IN nmol/g/h

| Experimental Group | 1 | 2 | 3 |
|---|---|---|---|
| [$^3$H] cholesterol oleate | + | + | + |
| Taurocholate | + | + | − |
| Heparin | − | + | − |
| EXP1 | 17.43 | 4.00 | 1.41 |
| EXP2 | 14.61 | 1.37 | 0.87 |
| EXP3 | 29.90 | 2.50 | 3.85 |
| AVERAGE = | 20.63 | 2.62 | 2.04 |
| N = | 3 | 3 | 3 |
| SD = | 8.14 | 1.32 | 1.59 |

The experimental procedure is the same as described in Example 3b. The intestine was washed with isotonic phosphate buffer without EGTA so the bound BAL was not removed from the intestine surface. Heparin (ICN Chemicals, Costa Mesa, Calif.) concentration in the uptake solution was 10 mg/ml.

(e) Addition of BAL to EGTA-treated intestine restored cholesterol uptake.

Materials and Reagents.

Native human milk bile salt-activated lipase (N-BAL) was purified as described in Wang and Johnson (1983), incorporated herein by reference. The recombinant truncated form of BAL (T-BAL, residues 1–538 lacking the carboxy terminal end) was prepared as described in Example 1, and reported by Downs et al., *Biochemistry* 33:7979–7985 (1994).

[1α-2α(n)-$^3$H] cholesterol oleate ($^3$H-cholesterol) was purchased from Amersham (Arlington Heights, Ill.). Other chemical reagents were purchased from Sigma Chemical Co, St. Louis, Mo.

A two-fold concentrated cholesterol oleate stock solution was prepared by emulsifying 6 μmol of $^3$H-cholesterol (1.6 μCi/μmol) and 0.6 μmol of dioleoyl-phosphatidylcholine 4 in 15 ml of isotonic sodium phosphate buffer, pH 7.4. The mixture was emulsified using a W-380 sonicator (Heat-system Ultrasonics, Inc., Farmingdale, N.Y.) at a setting of 5 (50% maximum output) for 30 seconds in an ice bath. After cooling, the mixture was further sonicated for an additional 30 seconds.

Methods.

In each of five experiments, three segments of rat small intestine (11 cm each) were washed once with isotonic buffer (pH 7.4), and the segments were ligated at both ends, with a catheter inserted into one end of each intestine segment for injection of solutions. One ml of isotonic phosphate buffer containing 1 mM EGTA to release BAL attached to the intestinal surface, as demonstrated in Example 1(a), was then injected into each intestinal segment. The segments were placed on a polystyrene weighing dish (14 cm square) containing 5 ml of the isotonic phosphate buffer to maintain moisture and incubated with gentle shaking for 30 minutes on top of an ice bath. After incubation, the intestinal segments were washed once with the EGTA-containing isotonic buffer, and twice with isotonic buffer containing 0.2 mM calcium chloride. One of the segments was then injected with 1 ml of the purified N-BAL, and the second segment was injected with 1 ml of T-BAL, with the average enzyme concentration of 0.8 mg/ml, in isotonic phosphate buffer and in the presence of 0.2 mM $Ca^{+2}$. The third intestinal segment, to which no BAL was added, was the control. These intestinal segments were then placed on the incubation tray again and incubated with gentle shaking for 30 minutes. After incubation, the solutions in the segments were removed and replaced with 1 ml [$^3$H] cholesterol oleate (0.2 mM) and 6 mM taurocholate in isotonic buffer. After incubation with shaking, as described above, the segments were then washed three times with isotonic phosphate buffer, and an 8 cm segment of each intestinal segment (about 0.7 g) was cut into 2 cm pieces, each of which was placed in 1 ml of 2% SDS-8M urea for solubilization of the tissue. To this mixture, 10 ml of Hydrocount™ was added and radioactivity was counted as described in Example 1(b).

The results are shown in Table IX.

TABLE IX

Cholesterol Uptake (nmol/g/h) in the Presence of Recombinant T-BAL.

| Exper. | Control | % of N-BAL* | +T-BAL | % of N-BAL* | +N-BAL | % |
|---|---|---|---|---|---|---|
| 1 | 5.28 | 64.86 | 4.61 | 56.63 | 8.14 | 100 |
| 2 | 4.24 | 38.23 | 6.43 | 57.98 | 11.09 | 100 |
| 3 | 5.52 | 44.12 | 9.78 | 78.18 | 12.51 | 100 |
| 4 | 4.91 | 57.49 | 4.34 | 50.82 | 8.54 | 100 |
| 5 | 13.85 | 43.62 | 11.42 | 35.97 | 31.75 | 100 |
| MEAN | 6.76 | 49.67 | 7.32 | 55.92 | 14.41 | 100 |
| SD | 3.99 | 11.07 | 3.16 | 15.20 | 9.86 | |
| SE | 1.79 | 4.95 | 1.41 | 6.80 | 4.41 | |

*N-BAL is native BAL purified from human milk; T-BAL is recombinant truncated BAL (without C-tail).

As shown in Table IX, cholesterol uptake was compared in EGTA-washed intestinal segments without added BAL (control), EGTA-washed segments treated with truncated BAL (+T-BAL), and EGTA-washed segments treated with purified native BAL (+N-BAL). Cholesterol uptake, measured in nmol cholesterol uptake/g intestine/hour, is shown in the left column of each group. The mean uptake values of the five experiments were Control 6.76, +T-BAL 7.32, and +BAL 14.41. The uptake in control segments represented non-specific trapping of radioactive cholesterol in intestinal segments caused, for example, by fusion of cholesterol micelles with intestinal cell membrane, and by residual intestinal BAL that remained after EGTA washing.

Because of the large deviation within each group due to biological differences among five rats, the data were calculated as percentage of +N-BAL group, and are presented in the right column of each group. The means of the percentage data show that uptake in Control was 49.67% and in +T-BAL was 55.92% of the +N-BAL group (100%). The difference between +N-BAL and +T-BAL uptake is statistically significant ($p < 0.005$).

If the Control data are subtracted from that of the T-BAL and that of the +N-BAL, the mean net uptakes are:

+T-BAL: 7.32−6.76=0.56 nmol/g/h

+N-BAL: 14.41−6.76=7.65 nmol/g/h

The net cholesterol uptake for +N-BAL is about fourteen times that for +T-BAL. The percentage difference of these two groups is also statistically highly significant ($p < 0.005$).

These results demonstrate that: (a) the reduced cholesterol uptake by EGTA- or EDTA-treated intestine is mediated by BAL loss, not by damage of cholesterol uptake machinery; and (b) the restoration of cholesterol uptake is due to the binding of the BAL carboxy terminal tail, which was lacking in the T-BAL, to the intestinal surface.

EXAMPLE 4

Addition of C-tail to intestinal content releases bound endogenous BAL.

Experiments were conducted to demonstrate that C-tail can compete for binding to intestinal surface CT-receptors resulting in the displacement of bound endogenous BAL.

(a) Preparation of C-tail.

A procedure has been devised to prepare pure C-tail of BAL from BAL. It should be noted that the purification of C-tail is very effective, so the starting BAL need not be completely homogeneous. BAL used in these C-tail isolation experiments was enriched by Heparin-Sepharose™ column (bed volume 14×1.5 cm) chromatography as described previously (Wang and Johnson (1983)). Three hundred ml of human skim milk was first centrifuged at 20,000 rpm for 2 h. The supernatant was filtered and applied onto the Heparin-Sepharose™ column which had been preequilibrated with 50 mM Tris-HCl buffer at pH 8.0. After loading, the column was washed with 200 ml of the equilibrating buffer and the BAL was eluted with 0.3M NaCl in the equilibrating buffer and collected in 5 ml fractions. The fractions was assayed for the esterase activity of BAL using p-nitrophenyl acetate as substrate. The fractions containing the BAL activity was pooled and dialyzed against distilled water and lyophilized. The yield was about 100 to 150 mg of dried materials from each batch. For the C-tail purification, a pooling from three batches of the partially purified BAL (about 350 mg) was first treated with 8M urea (10 mg/ml) for 2 h at room temperature and dialyzed against 50 mM Tris-HCl overnight. The denatured BAL was digested with trypsin and chymotrypsin (substrate:protease ratio of 50:1, w/w) for 4 h at 37° C. The same amounts of trypsin and chymotrypsin were added to this mixture for the second time and the incubation continued overnight at 37° C. The digest was then dialyzed against distilled water and lyophilized. The dried powder was dissolved in 5 ml of 70% formic acid and 50 mg of cyanogen bromide, sealed in a glass tube, and incubated at room temperature for overnight. The solution was diluted 10 times with distilled water and lyophilized. The material was further dissolved with distilled water and dialyzed and the insoluble material was removed by centrifugation. The soluble fraction was then lyophilized. The dried material was then solubilized with 3 ml of 50 mM Tris-HCl buffer containing 0.15M NaCl for gel-permeation chromatography using FPLC (fast protein liquid chromatography) using a two-tandem linked Sepharose™ column. One ml of sample was applied on the column for each run of chromatography. Carbohydrate analysis of the eluent fractions (Dubois et al., Anal. Chem. 28:350–356 (1956)) indicated that the tail was eluted at fractions of 21–25 (1 ml/fraction).

b) Structure and composition of C-tail.

N-terminal sequence and amino acid composition analyses of the material from the carbohydrate containing FPLC fractions indicated that the material corresponded to human BAL region containing residue of 528–712. As shown in Table X, the amino acid composition of the purified C-tail and the composition based on the known sequence are very similar. From the β-elimination experiment using alkali for the release of the O-linked oligosaccharide and in the further amino acid composition analysis of the sample, it was determined that between 8 to 10 residues of threonine were destroyed in each molecule of C-tail, while up to one residue of serine was destroyed by the same procedure. Therefore, it was concluded that most, if not all, of the oligosaccharides are attached to threonine residues in the C-tail.

TABLE X

The amino acid composition of isolated of the C-tail of human milk BAL and after treatment with alkali (0.1N NaOH).

| Amino Acid Residues | # residues (From known sequence) | # residues (Experimental) (Set Lysine = 1.0) | # residues (after β-elimination) |
|---|---|---|---|
| Lys | 1 | 1.0 | 1 |
| Asp | 18 | 17.8 | 20 |
| Thr | 23 | 22.4 | 14 |
| Ser | 15 | 13.5 | 14 |
| Glx | 6 | 6.1 | 8 |
| Pro | 60 | 56.9 | 60 |
| Gly | 26 | 25.6 | 28 |
| Ala | 18 | 17.9 | 20 |
| Val | 17 | 16.8 | 18 |
| Leu | 1 | 1.3 | 2 |
| | | | Total = 185 |

Calculated peptide M.W.=17,014

Data from the further analysis of the carbohydrate composition of the C-tail of human milk BAL based on the gas-liquid chromatography of the alditol acetate derivative (Griggs et al., Anal. Biochem. 43:369–381 (1971)) indicated the presence of fucose, galactose, galactosamine and glucosamine in the C-tail as shown in Table XI. Since galactosamine is the anchoring sugar for linking carbohydrate to the polypeptide chain from the ratio of lysine and galactosamine, it was estimated that there are about 8 to 10 oligosaccharides per C-tail molecule.

TABLE XI

Carbohydrate composition of C-tail of human milk BAL

| | μmol/mg | molar ratio |
|---|---|---|
| Fucose | 0.32 | 1.0 |
| Galactose | 0.95 | 3.0 |
| GlcNH$_2$ | 0.69 | 2.2 |
| GalNH$_2$ | 0.36 | 1.1 | c) C-tail causes the release of endogeneous BAL from rat intestine.

Experiments were carried out to determine whether isolated C-tail domain of human milk BAL can displace bound BAL from rat intestine surface. In these experiments, different amounts of C-tail were placed in the solutions contained inside of the ligated rat intestines. The BAL activity which was released after 30 minutes was determined.

The incubation of BAL intestine with EGTA and BAL C-tail and the determination of the BAL lipolytic activity in the eluate were as described in Example 3a and 3b.

The data are shown in Table XII. The results indicated that isolated C-tail is effective in displacing the bound endogeneous BAL from rat intestine.

TABLE XII

Release of endogeneous BAL from Rat intestine by EGTA and various doses of purified C-tail.

| | Isotonic buffer | EGTA | BAL C-tail (mg/ml) | | | | |
|---|---|---|---|---|---|---|---|
| | | | 0.05 | 0.1 | 0.2 | 0.5 | 1.0 |
| | Eluted BAL activity µmol/g intestine/h | | | | | | |
| | 13.00 | 253.20 | 107.80 | 30.00 | 149.30 | 96.00 | 65.80 |
| | 6.60 | 189.80 | 82.00 | 35.40 | 120.50 | 99.30 | 97.80 |
| | 6.90 | 169.60 | 131.10 | 97.50 | 190.10 | 379.00 | 274.10 |
| | 10.50 | 153.50 | 33.50 | 194.50 | 33.60 | 47.00 | 190.30 |
| | 6.80 | 105.50 | 95.00 | 60.00 | 245.30 | 269.00 | 193.71 |
| | 5.50 | 133.49 | 41.37 | 362.81 | 288.80 | 47.95 | 43.12 |
| Mean | 8.82 | 167.22 | 81.80 | 130.04 | 171.27 | 156.38 | 144.14 |
| SE | 1.18 | 20.85 | 15.54 | 52.68 | 37.27 | 55.64 | 36.50 |

EXAMPLE 5

The foregoing examples demonstrates that C-tail can elute the endogenously bound BAL from the rat intestinal surface. The following study demonstrates that the isolated C-tail can competitively inhibit cholesterol uptake in the rat intestine.

a) In vitro Inhibition of cholesterol uptake by the C-tail of BAL.

In the current study, three intestine segments were washed with isotonic phosphate buffer, pH 7.4. One of the intestine segment was incubated with the substrate [$^3$H] cholesterol oleate (0.2 mM) alone as control. The control intestine segment should have a higher rate of cholesterol uptake because the endogenous BAL on the intestinal surface is available for the transport of cholesterol. The second intestine segment was incubated with the same [$^3$H] cholesterol oleate and EGTA (1 mM). EGTA is known to elute endogenous BAL from the intestinal surface. The third intestine segment was incubated with the same [$^3$H] cholesterol oleate and the isolated C-tail (0.2 mg/ml).

Figure 4:
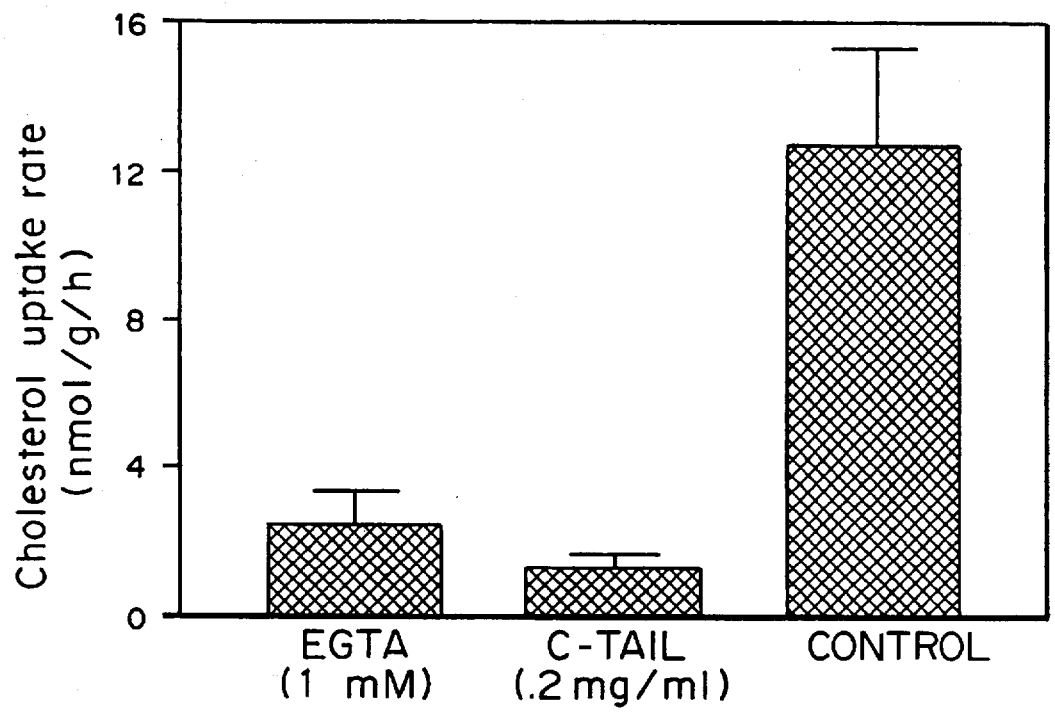
FIG. 4 is a graph showing the cholesterol uptake rate (nmol/g/h) for 1 mM EGTA, 0.2 mg/ml C-tail, and the control in rat intestine.

The data shown in the enclosed Table XIII are from 4 separate experiments. The averaged data are shown in FIG. 4. These results indicate that when C-tail is present, the cholesterol uptake is only about 10% of that of the control intestine. This compares favorably with the uptake of cholesterol when EGTA is present, which is about 18% of the control. These results demonstrate that the C-tail can effectively compete with the endogenous bound BAL for intestinal surface binding. The inhibition is due to the replacement of endogenous BAL on the intestinal surface by C tail, indicating that C-tail can be used to reduce the cholesterol uptake from human diet.

TABLE XIII

Reduction in Cholesterol Uptake.

| Final Conc. | EGTA (1 mM) | C-Tail (0.2 mg/ml) | Control |
|---|---|---|---|
| | 4.80 | 0.99 | 15.70 |
| | 0.34 | 1.17 | 17.80 |
| | 2.25 | 0.55 | 11.28 |
| | 2.20 | 2.30 | 6.43 |
| Average | 2.40 | 1.25 | 12.80 |
| SD | 1.83 | 0.75 | 5.04 |
| SE | 0.92 | 0.37 | 2.52 | b) In vivo Inhibition of cholesterol uptake by the C-tail of BAL.

Background.

The scheme of BAL's physiological function in cholesterol uptake by intestine, shown in FIG. 1, has been constructed based on data generated from in vitro experiments. In this scheme, BAL is first bound to the intestinal surface by putative receptors. The cholesterol or cholesterol esters is then transferred from hydrophobic food vesicles to the active site of the enzyme. Cholesterol ester is hydrolyzed in the BAL active site. The free cholesterol in the active site, whether the hydrolytic product or directly transferred from the vesicles, is transferred to the intestinal cells. This last step is assisted by the cell surface heparin, which possibly serves as an orientational factor. The results described above show that BAL not bound to intestinal surface is ineffective in mediating the uptake of cholesterol.

The scheme predicts that the feeding of isolated C-tail to live animals will compete for the putative receptor on the intestinal surface thus competitively inhibit cholesterol uptake. The following results confirm this prediction.

Experimental conditions.

Food (but not water) was withdrawn from a pair of adult white rats (average weight 259±27 g) 18 hour before the experiments. The experimental rat was tube fed with 1 ml solution containing 4 mg of isolated C-tail (from human milk BAL) 1% (wt./vol) glucose in isotonic phosphate buffer, pH 7.4. The control animal received the same volume of glucose-isotonic phosphate buffer without the C-tail. After 1 hour, both animals were tube fed with 1 ml of emulsified mixture containing 10 µCi [$^3$H]-cholesterol oleate plus cold cholesterol oleate with a final concentration of 0.2 mM, 4 mg of isolated C-tail, 0.2 mM triolein and 0.02 mM dioleoylphosphatidylcholine. The emulsification procedure was performed as described in section e) of Example 3 above. Again, the control animal received the same mixture but without C-tail. Blood samples were taken at 1 hour intervals for 5 hours in short term studies. Aliquots (100 µl) were taken from the blood and mixed with 2 ml of hepatane-isopropanol (3:7, vol/vol) followed by acidification with 1.25 ml of 0.033N $H_2SO_4$. The mixture was vortexed for 30 s and centrifuged at 4° C. for 10 min. Half of the upper phase (250 µl) was then utilized for counting the radioactivity.

The procedure for the isolation of C-tail from human milk BAL was performed as described above in section a) of Example 4. Based on the determined specific activity of the cholesterol oleate in the emulsion mixture of cholesterol oleate, the radioactivity in the blood was converted to the mass of cholesterol was transport from intestine into the blood compartment.

Results.

Rats were fasted for 18 hours to reduce the contents in the small intestine. Each experimental rat was tube fed with 4 mg. of isolated C-tail 1 hour before the administrating radioactive cholesterol oleate with another 4 mg. of C-tail. Control rats receive no C-tail but was otherwise treated identically to the experimental rats. Blood samples were taken at 1 hour intervals after the administration of cholesterol and determined for radioactivity.

Figure 5:
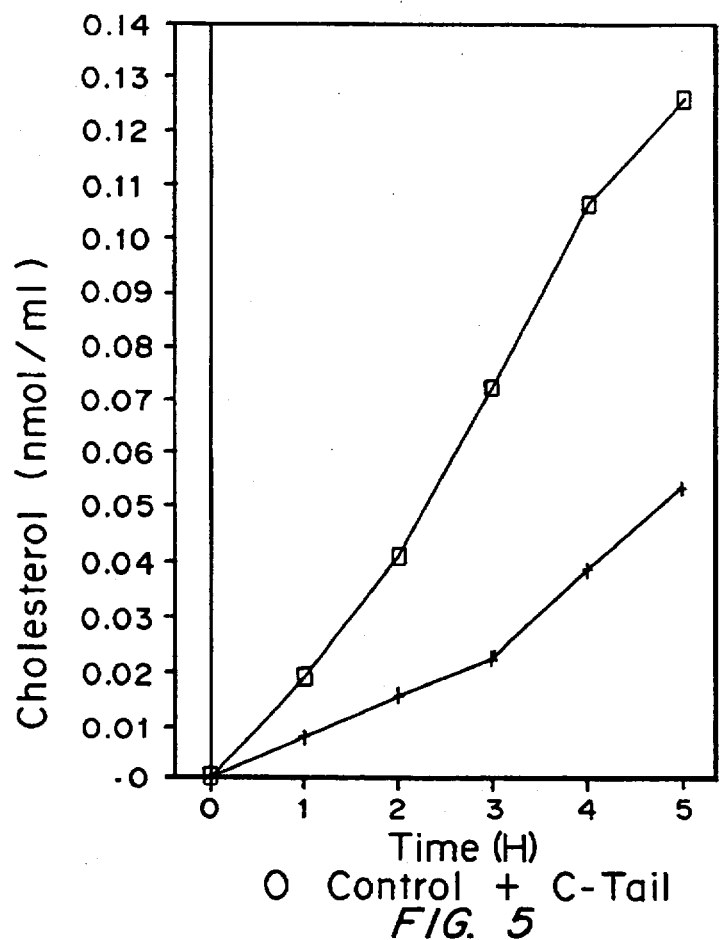
FIG. 5 is a graph showing blood [$^3$H]-cholesterol levels (nmol/mL) versus time (hours) in rats fed with [$^3$H]-cholesterol oleate, with and without C-tail. The blood [$^3$H]-cholesterol levels of a rat fed C-tail isolated from human milk BAL are indicated by crosses. The blood [$^3$H]-cholesterol levels of a rat not fed C-tail are indicated by squares. Blood samples were taken at 1 hour intervals up to 5 hours after the feeding of [$^3$H]-cholesterol oleate.
Figure 6:
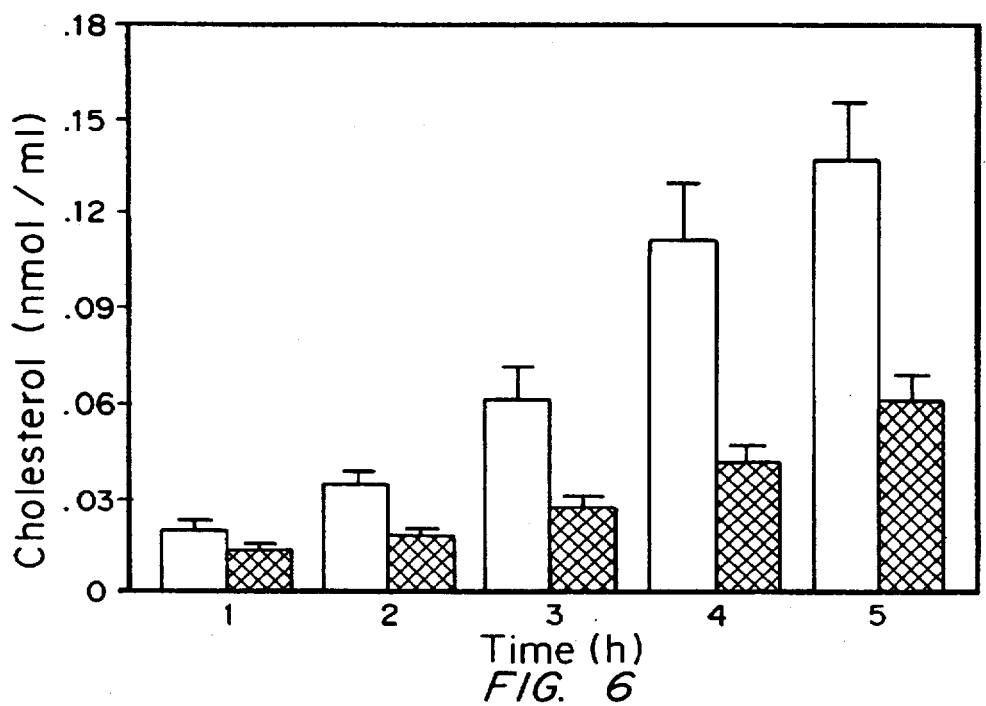
FIG. 6 is a graph of the averaged (from 6 experiments) levels of [$^3$H]-cholesterol in the blood (nmol/mL) versus time (hours) in rats fed with [$^3$H]-cholesterol oleate, with (shaded) or without (unshaded) isolated C-tail from human milk BAL. Blood samples were taken at 1 hour intervals up to 5 hours after the initial tube feeding of radiolabelled cholesterol oleate. The horizontal lines on top of the data bars represent the standard errors (see Table XIV).

FIG. 5 shows the results from a typical experiment of a single experimental rat and a control rat. Results have been obtained from a total of 6 control rats and 6 experimental rats. Table XIV shows the data from all 6 experiments and FIG. 6 shows the average cholesterol uptake of control group and experiment group receiving C-tail. The inhibition of cholesterol uptake by the administration of C-tail was 35%, 48.8%, 55.7%, 62.2% and 55.5% respectively for measurements taken at 1, 2, 3, 4 and 5 hours after the administration of radiolabeled cholesterol. As shown in Table XIV, the data between the control and experimental groups at 2, 3, 4 and 5 hour are statistically highly significant ($p<0.01$).

TABLE XIV

Appearance of Orally Fed Radiolabelled cholesterol in the Blood of Rats with and without Administration of C-tail Fragments.

| Expt. | Time/Hours (nmol/ml) | | | | |
|---|---|---|---|---|---|
| | 1 | 2 | 3 | 4 | 5 |
| Control | | | | | |
| 1 | 0.014 | 0.025 | 0.055 | 0.090 | 0.153 |
| 2 | 0.028 | 0.042 | 0.050 | 0.155 | 0.148 |
| 3 | 0.030 | 0.050 | 0.106 | 0.167 | 0.210 |
| 4 | 0.019 | 0.041 | 0.072 | 0.107 | 0.126 |
| 5 | 0.014 | 0.022 | 0.039 | 0.047 | 0.068 |
| 6 | 0.015 | 0.029 | 0.046 | 0.100 | 0.118 |
| Average | 0.020 | 0.035 | 0.061 | 0.111 | 0.137 |
| N = | 6 | 6 | 6 | 6 | 6 |
| SD | 0.007 | 0.011 | 0.024 | 0.044 | 0.047 |
| SE | 0.003 | 0.004 | 0.010 | 0.018 | 0.019 |
| C-Tail | | | | | |
| 1 | 0.012 | 0.014 | 0.020 | 0.044 | 0.085 |
| 2 | 0.019 | 0.024 | 0.035 | 0.059 | 0.074 |
| 3 | 0.009 | 0.017 | 0.040 | 0.048 | 0.072 |
| 4 | 0.008 | 0.016 | 0.022 | 0.038 | 0.053 |
| 5 | 0.011 | 0.021 | 0.025 | 0.040 | 0.053 |
| 6 | 0.016 | 0.014 | 0.019 | 0.025 | 0.029 |
| Average | 0.013 | 0.018 | 0.027 | 0.042 | 0.061 |
| N = | 6 | 6 | 6 | 6 | 6 |
| SD | 0.004 | 0.004 | 0.009 | 0.011 | 0.020 |
| SE | 0.002 | 0.002 | 0.004 | 0.005 | 0.008 |
| p Values | NS | 0.0052 | 0.0088 | 0.0042 | 0.0044 |

Note:
NS = not significant

Significance.

From these results, the following conclusions are derived:
(1) The inhibition of cholesterol uptake by C-tail in live rats supports the conclusion that the intestinal bound BAL mediates the cholesterol uptake.

(2) The fact that cholesterol uptake is inhibited by isolated C-tail indicate that (a) C-tail, either on BAL or isolated as a fragment by itself, binds to the same receptor on intestinal surface, (b) the binding of C-tail and receptor must be quite specific to achieve such a significant inhibition, and (c) the number of the receptors on the intestinal surface is limited. This is important because it indicates that reasonable levels of C-tail can have a significant effect on cholesterol uptake.

(3) These data from live animals substantiate the in vitro results which established that the C-tail, its equivalents from BAL of different animal species, recombinantly produced and chemically synthesized C-tail and its analogues, can effectively reduce cholesterol uptake. This supports the conclusion that use of C-tail in humans can reduce cardiovascular disease by reducing serum cholesterol levels due to dietary cholesterol.

(4) Many factors can be optimized to produce more efficient reduction of cholesterol uptake. For example, dosage of C-tail can be optimized, the pattern of C-tail administration can be altered to maximize its effect and time of C-tail administration as related to the cholesterol ingestion can be changed. Also, chemical modifications and physical modifications (additives and formulation) of C-tail can also be made to maximize the inhibition.

EXAMPLE 6

BAL mediates uptake of triglycerides but not taurocholate by isolated rat intestinal tissue.

The above examples establish that cholesterol uptake is mediated by BAL bound to intestinal surface. Since BAL also hydrolyses triglycerides and is activated by taurocholate, the example below addresses the question whether intestine bound BAL also mediates the uptake of triglycerides and taurocholate.

Experimental.

Triolein and taurocholate uptake experiments were performed in the same manner as the cholesterol uptake experiments described above except that $^3$H-radiolabelled trioleoylglycerol and $^4$C-taurocholate were used in place of cholesterol. In the triolein uptake experiments, either 6 mM or 30 mM of non-radiolabelled taurocholate was included with the radiolabelled triolein. Since the experimental system was isolated intestines, taurocholate was supplied to activate BAL. The emulsions of [$^3$H]-trioleoylglycerol (Amersham, Arlington Heights, Ill.) were prepared similarly as described previously (Downs et al. (1994). The 2-fold-concentrated substrate solution was prepared by emulsifying 15 µmol dioleoylphosphatidylcholine in 7.5 ml of isotonic phosphate buffer, pH 7.4. The mixture was emulsified using a W-380 sonicator (Heat Systems-Ultrasonics, Inc.) at a setting of 5 (50% maximum output) for 30 s in an ice bath. After cooling, the mixture was further sonicated for an additional 30 s. A volume of 1 ml of this emulsified solution was placed inside of isolated rat intestines for the measurement of uptake as described previously. For the studies of the uptake of taurocholate, a stock solution of taurocholate (6 mM) was made by including 2 µCi of tauro(carbonyl-$^{14}$) cholate and 30 µmol of taurocholate (Sigma) in 5 ml of isotonic phosphate buffer.

Results.

Figure 7:
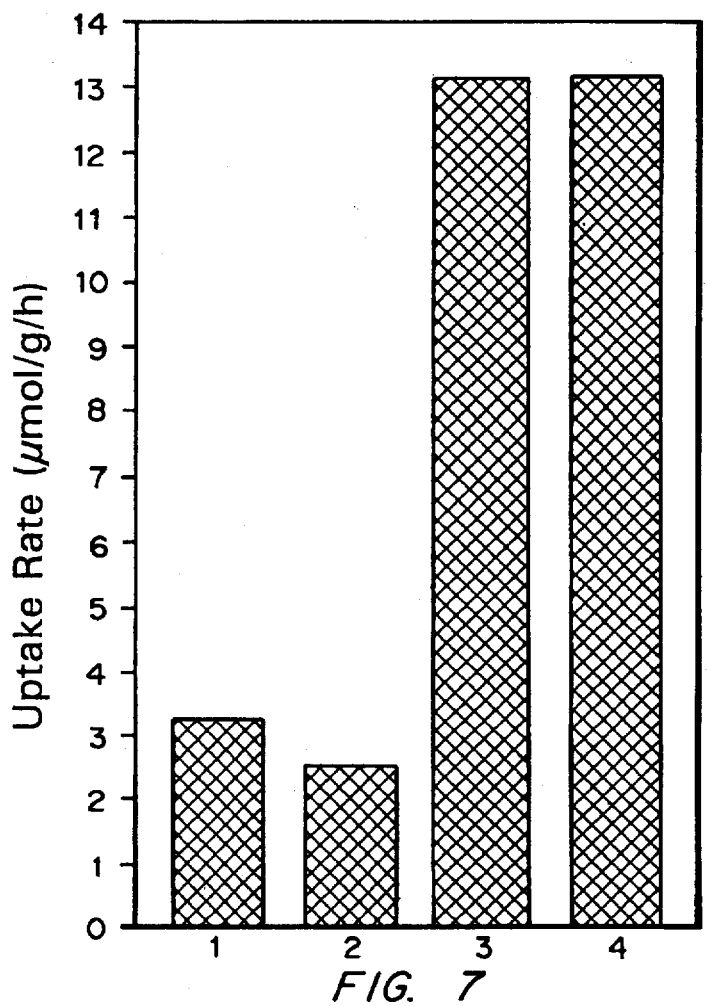
FIG. 7 is a graph of the rate of triolein uptake (μmol/g/h) in rats whose intestines were washed with 1) an EGTA solution, to remove bound BAL prior to the uptake experiment, with 6 mM taurocholate (column 1), 2) buffer, so the bound BAL was not removed, without taurocholate (column 2), 3) buffer with 6 mM taurocholate (column 3), and 4) buffer with 30 mM taurocholate (column 4). Data shown are the averages of results from 5 experiments (see Table XV). All 4 groups of animals received emulsified radiolabelled triolein.

The isolated rat intestines system, as described for the cholesterol uptake experiments in section b) of Example 2, was used to measure the uptake of fatty acids from triglycerides and taurocholate. From 5 experiments each, it was found that when BAL was removed from the intestinal surface by EGTA elution, the absorption of radioactive triolein was reduced by about 75% (Table XV and FIG. 7) with high statistical significance. Table XV shows that the inclusion of 6 mM of taurocholate is sufficient to keep a maximal uptake rate of triolein in the buffer washed intestines, since 30 mM taurocholate produced essentially the same uptake value (compare the last two columns in Table XV and columns 3 and 4 in FIG. 7). When taurocholate was not included, there was only baseline, uptake indicating that the process is mediated by BAL and that bile-salt activation is necessary for the uptake. The EGTA washed intestines, from which BAL was removed, had very low uptake (first data column in Table XV and column 1 in FIG. 7), which is near the baseline (second data column of 0 mM taurocholate in Table XV and column 2 in FIG. 7). These results indicate that BAL mediates the uptake of triolein.

TABLE XV

Triolein Uptake of Rat Intestine.

| | Intestine Treatments | | | |
|---|---|---|---|---|
| | EGTA | Buffer | Buffer | Buffer |
| | Taurocholate in Intestine | | | |
| | 6 mM | 0 mM | 6 mM | 30 mM |
| Experiment | | | | |
| 1 | 3.74 | 2.43 | 10.17 | 13.58 |
| 2 | 2.80 | 5.04 | 13.43 | 14.69 |
| 3 | 3.24 | 1.34 | 19.40 | 11.70 |
| 4 | 1.33 | 1.83 | 14.83 | 6.59 |
| 5 | 5.08 | 1.87 | 7.86 | 19.30 |
| Average | 3.24 | 2.50 | 13.14 | 13.17 |
| N | 5 | 5 | 5 | 5 |
| SD | 1.37 | 1.47 | 4.44 | 4.62 |
| SE | 0.61 | 0.66 | 1.99 | 2.07 |

Figure 8:
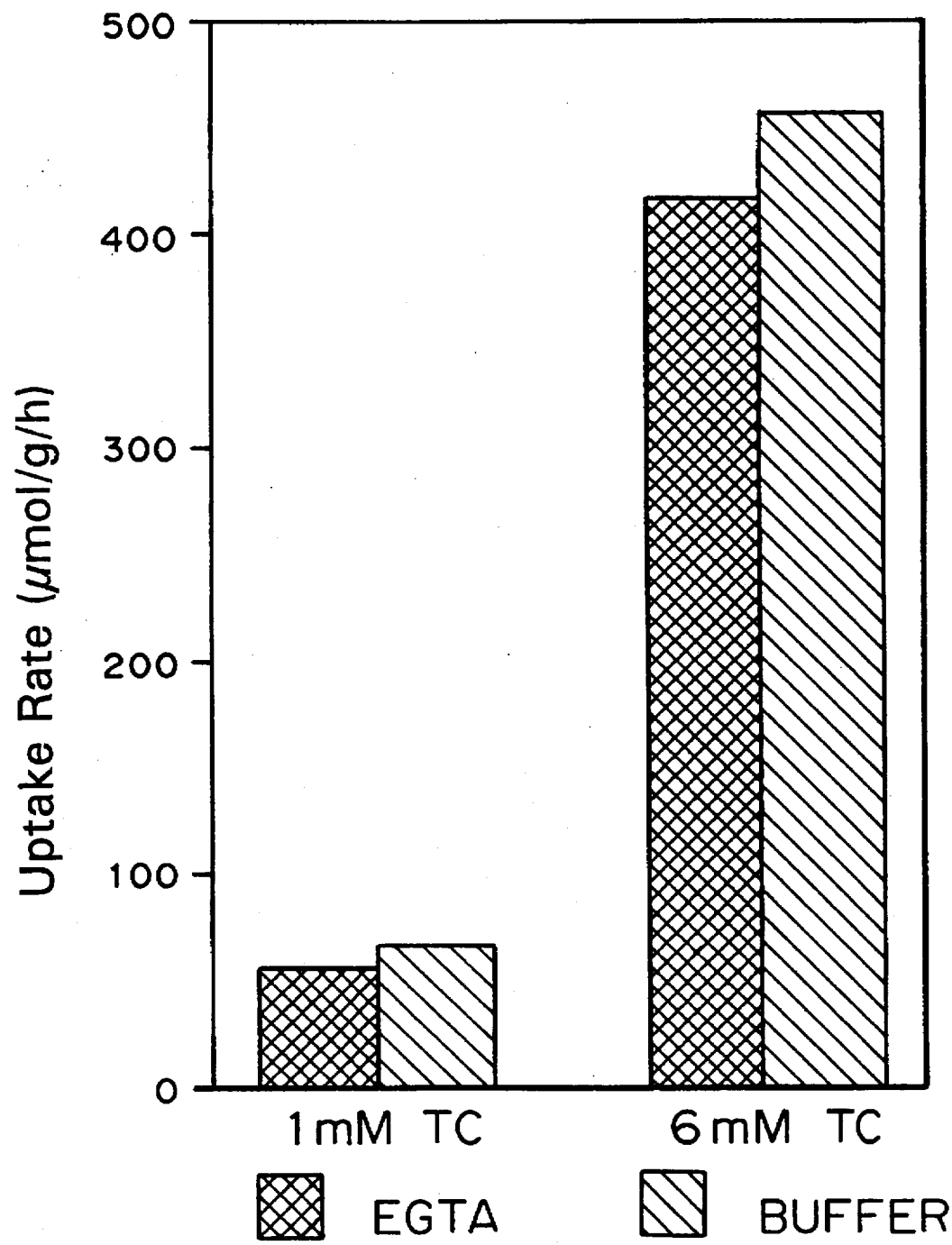
FIG. 8 is a graph of the rate of taurocholate uptake (μmol/g/h) in rats whose intestines were washed with 1) an EGTA solution, to remove bound BAL prior to the uptake experiment (cross shaded), and 2) buffer so the bound BAL was not removed (shaded). Data shown are the averages of results from 5 experiments (see Table XVI). The left and right pairs of columns show uptake rates from 1 mM and 6 mM radiolabelled taurocholate, respectively.

On the other hand, the removal of bound BAL from the intestinal surface did not change significantly the uptake of taurocholate (Table XVI and FIG. 8). The uptake of radio-labelled taurocholate was reduced only slightly when the intestine was washed with EGTA solutions to remove bound BAL prior to the uptake experiments. The small effect due to the EGTA elutions was not statistically significant.

TABLE XVI

Taurocholate Uptake by Rat Intestine.

| | Intestine Treatments | | | |
|---|---|---|---|---|
| | Control EGTA | Isotonic Buffer | Control EGTA | Isotonic Buffer |
| | Taurocholate conc. in intestine | | | |
| | 1 mM | | 6 mM | |
| Experiment | | | | |
| 1 | 42.00 | 64.00 | 279.00 | 392.00 |
| 2 | 69.91 | 95.77 | 461.49 | 503.27 |
| 3 | 45.36 | 51.56 | 385.45 | 501.75 |
| 4 | 52.51 | 53.84 | 362.86 | 440.18 |
| 5 | 62.28 | 60.45 | 336.84 | 392.48 |
| 6 | 60.94 | 65.32 | 678.95 | 513.32 |
| Average | 55.50 | 65.16 | 417.43 | 457.17 |
| SD | 10.74 | 15.96 | 141.42 | 56.5 |
| N | 6 | 6 | 6 | 6 |

Significance.

These results indicate that oral administration of the C-tail of BAL, recombinant C-tail and natural or chemically synthesized C-tail analogs shold be useful to reduce triglyceride absorption in humans, which should have medical or nutritional benefits.

Modifications and variations of the present invention will be obvious to those skilled in the art from the foregoing detailed description of the invention. Such modifications and variations are intended to come within the scope of the appended claims.

We claim:

1. A composition for reducing intestinal absorption of cholesterol comprising a polypeptide comprising at least four eleven amino acid repeats having at least three prolines present in the carboxy terminal region of human bile salt-activated lipase as shown in Sequence ID No. 1, that binds to a specific receptor on intestinal cells, wherein the polypeptide cannot hydrolyze cholesterol ester and is in an amount effective to reduce cholesterol uptake into the intestinal endothelium cells, in combination with a pharmaceutical carrier acceptable for oral administration.

2. The composition of claim 1 wherein the polypeptide comprises at least four eleven amino acid repeats present in amino acid residues 539 to 722 of Sequence ID No. 1.

3. The composition of claim 1 wherein the polypeptide further comprises the region of bile salt-activated lipase containing the catalytic site which has been inactivated.

4. The composition of claim 1 wherein the further comprises at least three of the repeating regions of the primate, human, cat, dog or rodent bile salt-activated lipase.

5. The composition of claim 1 wherein the polypeptide comprises at least ten eleven amino acid units having at least three prolines.

6. The composition of claim 1 wherein the carrier is a polymer or enteric encapsulating composition and the polypeptide is incorporated onto or within the carrier.

7. The composition of claim 1 wherein the polypeptide is in a dietary formulation for oral administration.

8. The composition of claim 1 wherein the polypeptide is in the milk of a transgenic cow or sheep.

9. The composition of claim 1 comprising the region of bile salt-activated lipase wherein the heparin binding site is unable to bind to heparin.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 722 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: internal ( x i ) SEQUENCE DESCRIPTION: SEQ ID NO:1:

```
Ala  Lys  Leu  Gly  Ala  Val  Tyr  Thr  Glu  Gly  Gly  Phe  Val  Glu  Gly  Val
 1              5                        10                       15

Asn  Lys  Lys  Leu  Gly  Leu  Leu  Gly  Asp  Ser  Val  Asp  Ile  Phe  Lys  Gly
                20                       25                       30

Ile  Pro  Phe  Ala  Ala  Pro  Thr  Lys  Ala  Leu  Glu  Asn  Pro  Gln  Pro  His
           35                       40                       45

Pro  Gly  Trp  Gln  Gly  Thr  Leu  Lys  Ala  Lys  Asn  Phe  Lys  Lys  Arg  Cys
     50                       55                       60

Leu  Gln  Ala  Thr  Ile  Thr  Gln  Asp  Ser  Thr  Tyr  Gly  Asp  Glu  Asp  Cys
65                       70                       75                       80
```

-continued

| | | | | | | | | | | | | | | |
|---|---|---|---|---|---|---|---|---|---|---|---|---|---|---|
|Leu|Tyr|Leu|Asn|Ile 85|Trp|Val|Pro|Gln 90|Gly|Arg|Lys|Gln|Val|Ser 95|Arg|
|Asp|Leu|Pro|Val 100|Met|Ile|Trp|Ile|Tyr 105|Gly|Gly|Ala|Phe|Leu 110|Met|Gly|
|Ser|Gly|His 115|Gly|Ala|Asn|Phe|Leu 120|Asn|Asn|Tyr|Leu|Tyr 125|Asp|Gly|Glu|
|Glu|Ile 130|Ala|Thr|Arg|Gly|Asn 135|Val|Ile|Val|Val|Thr 140|Phe|Asn|Tyr|Arg|
|Val 145|Gly|Pro|Leu|Gly|Phe 150|Leu|Ser|Thr|Gly|Asp 155|Ala|Asn|Leu|Pro|Gly 160|
|Asn|Tyr|Gly|Leu|Arg 165|Asp|Gln|His|Met|Ala 170|Ile|Ala|Trp|Val|Lys 175|Arg|
|Asn|Ile|Ala|Ala 180|Phe|Gly|Gly|Asp|Pro 185|Asn|Asn|Ile|Thr|Leu 190|Phe|Gly|
|Glu|Ser|Ala 195|Gly|Gly|Ala|Ser|Val 200|Ser|Leu|Gln|Thr|Leu 205|Ser|Pro|Tyr|
|Asn|Lys 210|Gly|Leu|Ile|Arg|Arg 215|Ala|Ile|Ser|Gln|Ser 220|Gly|Val|Ala|Leu|
|Ser 225|Pro|Trp|Val|Ile|Gln 230|Lys|Asn|Pro|Leu|Phe 235|Trp|Ala|Lys|Lys|Val 240|
|Ala|Glu|Lys|Val|Gly 245|Cys|Pro|Val|Gly|Asp 250|Ala|Ala|Arg|Met|Ala 255|Gln|
|Cys|Leu|Lys|Val 260|Thr|Asp|Pro|Arg|Ala 265|Leu|Thr|Leu|Ala|Tyr 270|Lys|Val|
|Pro|Leu|Ala 275|Gly|Leu|Glu|Tyr|Pro 280|Met|Leu|His|Tyr|Val 285|Gly|Phe|Val|
|Pro|Val 290|Ile|Asp|Gly|Asp|Phe 295|Ile|Pro|Ala|Asp|Pro 300|Ile|Asn|Leu|Tyr|
|Ala 305|Asn|Ala|Ala|Asp|Ile 310|Asp|Tyr|Ile|Ala|Gly 315|Thr|Asn|Asn|Met|Asp 320|
|Gly|His|Ile|Phe|Ala 325|Ser|Ile|Asp|Met|Pro 330|Ala|Ile|Asn|Lys|Gly 335|Asn|
|Lys|Lys|Val|Thr 340|Glu|Glu|Asp|Phe|Tyr 345|Lys|Leu|Val|Ser|Glu 350|Phe|Thr|
|Ile|Thr|Lys 355|Gly|Leu|Arg|Gly|Ala 360|Lys|Thr|Thr|Phe|Asp 365|Val|Tyr|Thr|
|Glu|Ser 370|Trp|Ala|Gln|Asp|Pro 375|Ser|Gln|Glu|Asn|Lys 380|Lys|Lys|Thr|Val|
|Val 385|Asp|Phe|Glu|Thr|Asp 390|Val|Leu|Phe|Leu|Val 395|Pro|Thr|Glu|Ile|Ala 400|
|Leu|Ala|Gln|His|Arg 405|Ala|Asn|Ala|Lys|Ser 410|Ala|Lys|Thr|Tyr|Ala 415|Tyr|
|Leu|Phe|Ser|His 420|Pro|Ser|Arg|Met|Pro 425|Val|Tyr|Pro|Lys|Trp 430|Val|Gly|
|Ala|Asp|His 435|Ala|Asp|Asp|Ile|Gln 440|Tyr|Val|Phe|Gly|Lys 445|Pro|Phe|Ala|
|Thr|Pro 450|Thr|Gly|Tyr|Arg|Pro 455|Gln|Asp|Arg|Thr|Val 460|Ser|Lys|Ala|Met|
|Ile 465|Ala|Tyr|Trp|Thr|Asn 470|Phe|Ala|Lys|Thr|Gly 475|Asp|Pro|Asn|Met|Gly 480|
|Asp|Ser|Ala|Val|Pro 485|Thr|His|Trp|Glu|Pro 490|Tyr|Thr|Thr|Glu|Asn 495|Ser|
|Gly|Tyr|Leu|Glu|Ile|Thr|Lys|Lys|Met|Gly|Ser|Ser|Met|Lys|Arg|

|       |       |       |       |       | 500   |       |       |       |       | 505   |       |       |       |       | 510   |       |       |       |
|-------|-------|-------|-------|-------|-------|-------|-------|-------|-------|-------|-------|-------|-------|-------|-------|-------|-------|-------|

Ser Leu Arg Thr Asn Phe Leu Arg Tyr Trp Thr Leu Thr Tyr Leu Ala
          515                     520                 525

Leu Pro Thr Val Thr Asp Gln Glu Ala Thr Pro Val Pro Pro Thr Gly
        530                     535                 540

Asp Ser Glu Ala Thr Pro Val Pro Pro Thr Gly Asp Ser Glu Thr Ala
545                     550                     555                     560

Pro Val Pro Pro Thr Gly Asp Ser Gly Ala Pro Pro Val Pro Pro Thr
                565                     570                     575

Gly Asp Ser Gly Ala Pro Pro Val Pro Thr Gly Asp Ser Gly Ala
            580                     585                 590

Pro Pro Val Pro Pro Thr Gly Asp Ser Gly Ala Pro Pro Val Pro Pro
        595                     600                 605

Thr Gly Asp Ser Gly Ala Pro Pro Val Pro Pro Thr Gly Asp Ser Gly
    610                     615                     620

Ala Pro Pro Val Pro Pro Thr Gly Asp Ser Gly Ala Pro Pro Val Pro
625                     630                     635                     640

Pro Thr Gly Asp Ala Gly Pro Pro Pro Val Pro Pro Thr Gly Asp Ser
                645                     650                     655

Gly Ala Pro Pro Val Pro Pro Thr Gly Asp Ser Gly Ala Pro Pro Val
            660                     665                     670

Thr Pro Thr Gly Asp Ser Glu Thr Ala Pro Val Pro Pro Thr Gly Asp
        675                     680                     685

Ser Gly Ala Pro Pro Val Pro Pro Thr Gly Asp Ser Glu Ala Ala Pro
    690                     695                     700

Val Pro Pro Thr Asp Asp Ser Lys Glu Ala Gln Met Pro Ala Val Ile
705                     710                     715                     720

Arg Phe ( 2 ) INFORMATION FOR SEQ ID NO:2:

( i ) SEQUENCE CHARACTERISTICS:
        ( A ) LENGTH: 742 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: internal ( i x ) FEATURE:
        ( A ) NAME/KEY: Modified-site
        ( B ) LOCATION: 186..187
        ( D ) OTHER INFORMATION: /note= "Position 187 represents a
            potential N- linked glycosylation site."

( i x ) FEATURE:
        ( A ) NAME/KEY: Modified-site
        ( B ) LOCATION: 193..194
        ( D ) OTHER INFORMATION: /note= "The serine at position 194
            represents an active site serine."

( i x ) FEATURE:
        ( A ) NAME/KEY: misc. feature
        ( B ) LOCATION: 1..742
        ( D ) OTHER INFORMATION: /Function = "Amino acid sequence for
            the Human Milk Bile Salt-activated Lipase."

( x i ) SEQUENCE DESCRIPTION: SEQ ID NO:2:

Met Gly Arg Leu Gln Leu Val Val Leu Gly Leu Thr Cys Cys Trp Ala
1                   5                   10                  15

-continued

| | | | | | | | | | | | | | | |
|---|---|---|---|---|---|---|---|---|---|---|---|---|---|---|
| Val | Ala | Ser | Ala | Ala | Lys | Leu | Gly | Ala | Val | Tyr | Thr | Glu | Gly | Gly | Phe |
| | | | 20 | | | | 25 | | | | | 30 | | | |
| Val | Glu | Gly | Val | Asn | Lys | Lys | Leu | Gly | Leu | Leu | Gly | Asp | Ser | Val | Asp |
| | | 35 | | | | 40 | | | | | 45 | | | | |
| Ile | Phe | Lys | Gly | Ile | Pro | Phe | Ala | Ala | Pro | Thr | Lys | Ala | Leu | Glu | Asn |
| | 50 | | | | 55 | | | | | 60 | | | | | |
| Pro | Gln | Pro | His | Pro | Gly | Trp | Gln | Gly | Thr | Leu | Lys | Ala | Lys | Asn | Phe |
| 65 | | | | 70 | | | | | 75 | | | | | | 80 |
| Lys | Lys | Arg | Cys | Leu | Gln | Ala | Thr | Ile | Thr | Gln | Asp | Ser | Thr | Tyr | Gly |
| | | | 85 | | | | | 90 | | | | | | 95 | |
| Asp | Glu | Asp | Cys | Leu | Tyr | Leu | Asn | Ile | Trp | Val | Pro | Gln | Gly | Arg | Lys |
| | | | 100 | | | | | 105 | | | | 110 | | | |
| Gln | Val | Ser | Arg | Asp | Leu | Pro | Val | Met | Ile | Trp | Ile | Tyr | Gly | Gly | Ala |
| | | 115 | | | | | 120 | | | | | 125 | | | |
| Phe | Leu | Met | Gly | Ser | Gly | His | Gly | Ala | Asn | Phe | Leu | Asn | Asn | Tyr | Leu |
| | 130 | | | | | 135 | | | | | 140 | | | | |
| Tyr | Asp | Gly | Glu | Glu | Ile | Ala | Thr | Arg | Gly | Asn | Val | Ile | Val | Val | Thr |
| 145 | | | | | 150 | | | | | 155 | | | | | 160 |
| Phe | Asn | Tyr | Arg | Val | Gly | Pro | Leu | Gly | Phe | Leu | Ser | Thr | Gly | Asp | Ala |
| | | | | 165 | | | | | 170 | | | | | 175 | |
| Asn | Leu | Pro | Gly | Asn | Tyr | Gly | Leu | Arg | Asp | Gln | His | Met | Ala | Ile | Ala |
| | | | 180 | | | | | 185 | | | | | 190 | | |
| Trp | Val | Lys | Arg | Asn | Ile | Ala | Ala | Phe | Gly | Gly | Asp | Pro | Asn | Asn | Ile |
| | | 195 | | | | | 200 | | | | | 205 | | | |
| Thr | Leu | Phe | Gly | Glu | Ser | Ala | Gly | Gly | Ala | Ser | Val | Ser | Leu | Gln | Thr |
| | 210 | | | | | 215 | | | | | 220 | | | | |
| Leu | Ser | Pro | Tyr | Asn | Lys | Gly | Leu | Ile | Arg | Arg | Ala | Ile | Ser | Gln | Ser |
| 225 | | | | | 230 | | | | | 235 | | | | | 240 |
| Gly | Val | Ala | Leu | Ser | Pro | Trp | Val | Ile | Gln | Lys | Asn | Pro | Leu | Phe | Trp |
| | | | | 245 | | | | | 250 | | | | | 255 | |
| Ala | Lys | Lys | Val | Ala | Glu | Lys | Val | Gly | Cys | Pro | Val | Gly | Asp | Ala | Ala |
| | | | 260 | | | | | 265 | | | | | 270 | | |
| Arg | Met | Ala | Gln | Cys | Leu | Lys | Val | Thr | Asp | Pro | Arg | Ala | Leu | Thr | Leu |
| | | 275 | | | | | 280 | | | | | 285 | | | |
| Ala | Tyr | Lys | Val | Pro | Leu | Ala | Gly | Leu | Glu | Tyr | Pro | Met | Leu | His | Tyr |
| | 290 | | | | | 295 | | | | | 300 | | | | |
| Val | Gly | Phe | Val | Pro | Val | Ile | Asp | Gly | Asp | Phe | Ile | Pro | Ala | Asp | Pro |
| 305 | | | | | 310 | | | | | 315 | | | | | 320 |
| Ile | Asn | Leu | Tyr | Ala | Asn | Ala | Ala | Asp | Ile | Asp | Tyr | Ile | Ala | Gly | Thr |
| | | | | 325 | | | | | 330 | | | | | 335 | |
| Asn | Asn | Met | Asp | Gly | His | Ile | Phe | Ala | Ser | Ile | Asp | Met | Pro | Ala | Ile |
| | | | 340 | | | | | 345 | | | | | 350 | | |
| Asn | Lys | Gly | Asn | Lys | Lys | Val | Thr | Glu | Glu | Asp | Phe | Tyr | Lys | Leu | Val |
| | | 355 | | | | | 360 | | | | | 365 | | | |
| Ser | Glu | Phe | Thr | Ile | Thr | Lys | Gly | Leu | Arg | Gly | Ala | Lys | Thr | Thr | Phe |
| | 370 | | | | | 375 | | | | | 380 | | | | |
| Asp | Val | Tyr | Thr | Glu | Ser | Trp | Ala | Gln | Asp | Pro | Ser | Gln | Glu | Asn | Lys |
| 385 | | | | | 390 | | | | | 395 | | | | | 400 |
| Lys | Lys | Thr | Val | Val | Asp | Phe | Glu | Thr | Asp | Val | Leu | Phe | Leu | Val | Pro |
| | | | | 405 | | | | | 410 | | | | | 415 | |
| Thr | Glu | Ile | Ala | Leu | Ala | Gln | His | Arg | Ala | Asn | Ala | Lys | Ser | Ala | Lys |
| | | | 420 | | | | | 425 | | | | | 430 | | |
| Thr | Tyr | Ala | Tyr | Leu | Phe | Ser | His | Pro | Ser | Arg | Met | Pro | Val | Tyr | Pro |
| | | 435 | | | | | 440 | | | | | 445 | | | |

| | | | | | | | | | | | | | |
|---|---|---|---|---|---|---|---|---|---|---|---|---|---|
| Lys | Trp<br>450 | Val | Gly | Ala | Asp | His<br>455 | Ala | Asp | Asp | Ile<br>460 | Gln | Tyr | Val | Phe | Gly |
| Lys<br>465 | Pro | Phe | Ala | Thr | Pro<br>470 | Thr | Gly | Tyr | Arg | Pro<br>475 | Gln | Asp | Arg | Thr | Val<br>480 |
| Ser | Lys | Ala | Met | Ile<br>485 | Ala | Tyr | Trp | Thr | Asn<br>490 | Phe | Ala | Lys | Thr | Gly<br>495 | Asp |
| Pro | Asn | Met | Gly<br>500 | Asp | Ser | Ala | Val | Pro<br>505 | Thr | His | Trp | Glu | Pro<br>510 | Tyr | Thr |
| Thr | Glu | Asn<br>515 | Ser | Gly | Tyr | Leu | Glu<br>520 | Ile | Thr | Lys | Lys | Met<br>525 | Gly | Ser | Ser |
| Ser | Met<br>530 | Lys | Arg | Ser | Leu | Arg<br>535 | Thr | Asn | Phe | Leu | Arg<br>540 | Tyr | Trp | Thr | Leu |
| Thr<br>545 | Tyr | Leu | Ala | Leu | Pro<br>550 | Thr | Val | Thr | Asp | Gln<br>555 | Glu | Ala | Thr | Pro | Val<br>560 |
| Pro | Pro | Thr | Gly | Asp<br>565 | Ser | Glu | Ala | Thr | Pro<br>570 | Val | Pro | Pro | Thr | Gly<br>575 | Asp |
| Ser | Glu | Thr | Ala<br>580 | Pro | Val | Pro | Pro | Thr<br>585 | Gly | Asp | Ser | Gly | Ala<br>590 | Pro | Pro |
| Val | Pro | Pro<br>595 | Thr | Gly | Asp | Ser | Gly<br>600 | Ala | Pro | Pro | Val | Pro<br>605 | Pro | Thr | Gly |
| Asp | Ser<br>610 | Gly | Ala | Pro | Pro | Val<br>615 | Pro | Pro | Thr | Gly | Asp<br>620 | Ser | Gly | Ala | Pro |
| Pro<br>625 | Val | Pro | Pro | Thr | Gly<br>630 | Asp | Ser | Gly | Ala | Pro<br>635 | Pro | Val | Pro | Pro | Thr<br>640 |
| Gly | Asp | Ser | Gly | Ala<br>645 | Pro | Pro | Val | Pro | Pro<br>650 | Thr | Gly | Asp | Ser | Gly<br>655 | Ala |
| Pro | Pro | Val | Pro<br>660 | Pro | Thr | Gly | Asp | Ala<br>665 | Gly | Pro | Pro | Pro | Val<br>670 | Pro | Pro |
| Thr | Gly | Asp<br>675 | Ser | Gly | Ala | Pro | Pro<br>680 | Val | Pro | Pro | Thr | Gly<br>685 | Asp | Ser | Gly |
| Ala | Pro<br>690 | Pro | Val | Thr | Pro | Thr<br>695 | Gly | Asp | Ser | Glu | Thr<br>700 | Ala | Pro | Val | Pro |
| Pro<br>705 | Thr | Gly | Asp | Ser | Gly<br>710 | Ala | Pro | Pro | Val | Pro<br>715 | Pro | Thr | Gly | Asp | Ser<br>720 |
| Glu | Ala | Ala | Pro | Val<br>725 | Pro | Pro | Thr | Asp | Asp<br>730 | Ser | Lys | Glu | Ala | Gln<br>735 | Met |
| Pro | Ala | Val | Ile<br>740 | Arg | Phe | | | | | | | | | | |

( 2 ) INFORMATION FOR SEQ ID NO:3:

( i ) SEQUENCE CHARACTERISTICS:
        ( A ) LENGTH: 3018 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc. feature
        ( B ) LOCATION: 1..742
        ( D ) OTHER INFORMATION: /Function = "Nucleotides 679 through 2904 encode the amino acid sequence for the Human Milk Bile Salt- activated Lipase."

( x i ) SEQUENCE DESCRIPTION: SEQ ID NO:3:

| | | | | | | |
|---|---|---|---|---|---|---|
| CTCAATTGGA | GGATCAAAGT | TGAGAAAAGT | AATATTCGAC | ATTTTTCGAT | TCAACGGAGT | 60 |
| GGCCACCAAG | ACGATGTCAT | AGAAGTCTGA | ACGAGTCTCA | GTTCCAATTT | GGTAGACCAC | 120 |
| TTCATACATC | TTTGTTGGAT | TTCCTGTGTA | CTTGGTCTTT | GTTTCTCCT | CGATGTACAT | 180 |
| TACTGAGCCA | GATATAAGAT | TGCTTTTGGA | TGCCTGCAGA | AGCCCTGAGC | AAACAAGTTT | 240 |
| ATTGCCACCT | TCTACTGCCC | AAAGGCCAGA | ATCAGAACAG | GACAGTGACA | CCGCCCCAC | 300 |
| AAAGGCATTG | ATGTCCGTGC | TTTGGCCATA | ATTGACCCTC | ATAACAGGAG | CAATCATTTC | 360 |
| ATTGAGGAAC | TTCTCAGAAA | AGCCGGCCTT | TTGCAAGGTT | TCAAGAAGTG | TTCGATTAAG | 420 |
| CATTCCAAGG | AAGTCATCTC | CTCCTAGAGC | ATGAAGTAAT | TTTTCGACAC | TACTGAAGGC | 480 |
| ATAGTCATGA | GACTGGTAGC | GGTAGATCCT | CATGAACTTG | TCTAACACGT | CCTCTACCCA | 540 |
| CATGTGCATA | CGGAGGGATT | GAAATCCATA | GCGCCAAACT | AATTTAATCA | CGTTAATTAT | 600 |
| GAACCAGTTG | CTCTCCTCAA | ATACCAGAGT | CTCTCCATTA | TATATCCCCA | GTAGGCCACC | 660 |
| CAGAGGCTGA | TGCTCACCAT | GGGGCGCCTG | CAACTGGTTG | TGTTGGGCCT | CACCTGCTGC | 720 |
| TGGGCAGTGG | CGAGTGCCGC | GAAGCTGGGC | GCCGTGTACA | CAGAAGGTGG | GTTCGTGGAA | 780 |
| GGCGTCAATA | GAAGCTCGG | CCTCCTGGGT | GACTCTGTGG | ACATCTTCAA | GGGCATCCCC | 840 |
| TTCGCAGCTC | CCACCAAGGC | CCTGGAAAAT | CCTCAGCCAC | ATCCTGGCTG | GCAAGGGACC | 900 |
| CTGAAGGCCA | GAACTTCAA | GAAGAGATGC | CTGCAGGCCA | CCATCACCCA | GGACAGCACC | 960 |
| TACGGGGATG | AAGACTGCCT | GTACCTCAAC | ATTTGGGTGC | CCAGGGCAG | GAAGCAAGTC | 1020 |
| TCCCGGGACC | TGCCCGTTAT | GATCTGGATC | TATGGAGGCG | CCTTCCTCAT | GGGGTCCGGC | 1080 |
| CATGGGGCCA | ACTTCCTCAA | CAACTACCTG | TATGACGGCG | AGGAGATCGC | CACACGCGGA | 1140 |
| AACGTCATCG | TGGTCACCTT | CAACTACCGT | GTCGGCCCCC | TTGGGTTCCT | CAGCACTGGG | 1200 |
| GACGCCAATC | TGCCAGGTAA | CTATGGTCTT | CGGGATCAGC | ACATGGCCAT | TGCTTGGGTG | 1260 |
| AAGAGGAATA | TCGCGGCCTT | CGGGGGGGAC | CCCAACAACA | TCACGCTCTT | CGGGGAGTCT | 1320 |
| GCTGGAGGTG | CCAGCGTCTC | TCTGCAGACC | CTCTCCCCCT | ACAACAAGGG | CCTCATCCGG | 1380 |
| CGAGCCATCA | GCCAGAGCGG | CGTGGCCCTG | AGTCCCTGGG | TCATCCAGAA | AAACCCACTC | 1440 |
| TTCTGGGCCA | AAAAGGTGGC | TGAGAAGGTG | GGTTGCCCTG | TGGGTGATGC | CGCCAGGATG | 1500 |
| GCCCAGTGTC | TGAAGGTTAC | TGATCCCCGA | GCCCTGACGC | TGGCCTATAA | GGTGCCGCTG | 1560 |
| GCAGGCCTGG | AGTACCCCAT | GCTGCACTAT | GTGGGCTTCG | TCCCTGTCAT | TGATGGAGAC | 1620 |
| TTCATCCCCG | CTGACCCGAT | CAACCTGTAC | GCCAACGCCG | CCGACATCGA | CTATATAGCA | 1680 |
| GGCACCAACA | ACATGGACGG | CCACATCTTC | GCCAGCATCG | ACATGCCTGC | CATCAACAAG | 1740 |
| GGCAACAAGA | AACTCACGGA | GGAGGACTTC | TACAAGCTGG | TCAGTGAGTT | CACAATCACC | 1800 |
| AAGGGGCTCA | GAGGCGCCAA | GACGACCTTT | GATGTCTACA | CCGAGTCCTG | GGCCCAGGAC | 1860 |
| CCATCCCAGG | AGAATAAGAA | GAAGACTGTG | GTGGACTTTG | AGACCGATGT | CCTCTTCCTG | 1920 |
| GTGCCCACCG | AGATTGCCCT | AGCCCAGCAC | AGAGCCAATG | CCAAGAGTGC | CAAGACCTAC | 1980 |
| GCCTACCTGT | TTTCCCATCC | CTCTCGGATG | CCCGTCTACC | CAAATGGGT | GGGGCCGAC | 2040 |
| CATGCAGATG | ACATTCAGTA | CGTTTTCGGG | AAGCCCTTCG | CCACCCCCAC | GGGCTACCGG | 2100 |
| CCCCAAGACA | GGACAGTCTC | TAAGGCCATG | ATCGCCTACT | GGACCAACTT | TGCCAAAACA | 2160 |
| GGGGACCCCA | ACATGGGCGA | CTCGGCTGTG | CCCACACACT | GGAACCCTA | CACTACGGAA | 2220 |
| AACAGCGGCT | ACCTGGAGAT | CACCAAGAAG | ATGGGCAGCA | GCTCCATGAA | GCGGAGCCTG | 2280 |
| AGAACCAACT | TCCTGCGCTA | CTGGACCCTC | ACCTATCTGG | CGCTGCCCAC | AGTGACCGAC | 2340 |

| | | | | | |
|---|---|---|---|---|---|
| CAGGAGGCCA | CCCCTGTGCC | CCCCACAGGG | GACTCCGAGG | CCACTCCCGT | GCCCCCCACG | 2400
| GGTGACTCCG | AGACCGCCCC | CGTGCCGCCC | ACGGGTGACT | CCGGGGCCCC | CCCCGTGCCG | 2460
| CCCACGGGTG | ACTCCGGGGC | CCCCCCCGTG | CCGCCCACGG | GTGACTCCGG | GGCCCCCCCC | 2520
| GTGCCGCCCA | CGGGTGACTC | CGGGGCCCCC | CCCGTGCCGC | CCACGGGTGA | CTCCGGGGCC | 2580
| CCCCCGTGC | CGCCCACGGG | TGACTCCGGG | GCCCCCCCG | TGCCGCCCAC | GGGTGACTCC | 2640
| GGCGCCCCC | CCGTGCCGCC | CACGGGTGAC | GCCGGGCCCC | CCCCGTGCC | GCCCACGGGT | 2700
| GACTCCGGCG | CCCCCCCGT | GCCGCCCACG | GGTGACTCCG | GGGCCCCCCC | CGTGACCCCC | 2760
| ACGGGTGACT | CCGAGACCGC | CCCCGTGCCG | CCCACGGGTG | ACTCCGGGGC | CCCCCCTGTG | 2820
| CCCCCCACGG | GTGACTCTGA | GGCTGCCCCT | GTGCCCCCA | CAGATGACTC | CAAGGAAGCT | 2880
| CAGATGCCTG | CAGTCATTAG | GTTTTAGCGT | CCCATGAGCC | TTGGTATCAA | GAGGCCACAA | 2940
| GAGTGGGACC | CCAGGGGCTC | CCCTCCCATC | TTGAGCTCTT | CCTGAATAAA | GCCTCATACC | 3000
| CCTGAAAAAA | AAAAAAA | | | | | 3018

( 2 ) INFORMATION FOR SEQ ID NO:4:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( i x ) FEATURE:
( A ) NAME/KEY: misc. feature
( B ) LOCATION: 1..21
( D ) OTHER INFORMATION: /Function = "Primer."

( x i ) SEQUENCE DESCRIPTION: SEQ ID NO:4:

CATATGGCGA AGCTGGGCGC C    21

( 2 ) INFORMATION FOR SEQ ID NO:5:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( i x ) FEATURE:
( A ) NAME/KEY: misc. feature
( B ) LOCATION: 1..24
( D ) OTHER INFORMATION: /Function = "Primer."

( x i ) SEQUENCE DESCRIPTION: SEQ ID NO:5:

GGATCCTTAG GTGGCCTCCT GGTCG    25

( 2 ) INFORMATION FOR SEQ ID NO:6:

( i ) SEQUENCE CHARACTERISTICS:
( A ) LENGTH: 11 amino acids
( B ) TYPE: amino acid
( D ) TOPOLOGY: linear

```
        ( i i ) MOLECULE TYPE: protein ( i i i ) HYPOTHETICAL: NO ( v ) FRAGMENT TYPE: internal ( i x ) FEATURE:
                ( A ) NAME/KEY: misc. feature
                ( B ) LOCATION: 1..11
                ( D ) OTHER INFORMATION: /Function = "Concensus Sequence."

( x i ) SEQUENCE DESCRIPTION: SEQ ID NO:6:

Pro  Val  Pro  Pro  Thr  Gly  Asp  Ser  Gly  Ala  Pro
              5                        10
```